US008722395B2

(12) United States Patent
Nazareth et al.

(10) Patent No.: US 8,722,395 B2
(45) Date of Patent: *May 13, 2014

(54) ELECTRONIC ANALYTE ASSAYING DEVICE

(75) Inventors: Albert R. Nazareth, Mercerville, NJ (US); Francis T. Delahanty, Washington Crossing, PA (US); Gregory M. Bandru, Ewing, NJ (US); Henry J. Wieck, Plainsboro, NJ (US); Stephen R. Synakowski, Dewitt, NY (US)

(73) Assignee: Church & Dwight Co., Inc., Princeton, NJ (US)

( * ) Notice: Subject to any disclaimer, the term of this patent is extended or adjusted under 35 U.S.C. 154(b) by 382 days.

This patent is subject to a terminal disclaimer.

(21) Appl. No.: 12/793,577

(22) Filed: Jun. 3, 2010

(65) Prior Publication Data
US 2010/0239460 A1    Sep. 23, 2010

Related U.S. Application Data

(63) Continuation of application No. 10/888,676, filed on Jul. 9, 2004, now Pat. No. 7,763,454.

(51) Int. Cl.
*C12M 1/34* (2006.01)

(52) U.S. Cl.
USPC ...................................... 435/287.7

(58) Field of Classification Search
None
See application file for complete search history.

(56) References Cited

U.S. PATENT DOCUMENTS

| | | | |
|---|---|---|---|
| 3,892,492 A | 7/1975 | Eichenberger | |
| 3,910,701 A | 10/1975 | Henderson et al. | |
| 4,203,724 A | 5/1980 | Sawai et al. | |
| 4,637,403 A | 1/1987 | Garcia et al. | |
| 4,676,653 A | 6/1987 | Strohmeier et al. | |
| 4,685,059 A | 8/1987 | Yamamoto | |
| 4,717,545 A * | 1/1988 | Morris | 422/401 |
| 4,755,058 A * | 7/1988 | Shaffer | 356/408 |
| 4,787,398 A * | 11/1988 | Garcia et al. | 600/583 |
| 4,791,461 A | 12/1988 | Kishimoto et al. | |
| 4,935,346 A | 6/1990 | Phillips et al. | |
| 5,059,394 A | 10/1991 | Phillips et al. | |
| 5,073,029 A | 12/1991 | Eberly et al. | |
| 5,141,850 A | 8/1992 | Cole et al. | |
| 5,145,789 A | 9/1992 | Corti et al. | |
| 5,179,005 A | 1/1993 | Phillips et al. | |
| 5,246,858 A | 9/1993 | Arbuckle et al. | |
| 5,279,294 A | 1/1994 | Anderson et al. | |
| 5,281,395 A | 1/1994 | Markart et al. | |
| 5,371,020 A | 12/1994 | Frischauf | |
| 5,418,136 A | 5/1995 | Miller et al. | |
| 5,477,326 A * | 12/1995 | Dosmann | 356/406 |
| 5,507,410 A * | 4/1996 | Clark et al. | 221/171 |
| 5,580,794 A | 12/1996 | Allen | |
| 5,602,040 A | 2/1997 | May et al. | |
| 5,622,871 A | 4/1997 | May et al. | |
| 5,695,949 A | 12/1997 | Galen et al. | |
| 5,728,352 A | 3/1998 | Poto et al. | |
| 5,739,041 A | 4/1998 | Nazareth et al. | |
| D394,317 S | 5/1998 | Carp | |
| 5,795,543 A | 8/1998 | Poto et al. | |
| 5,837,546 A | 11/1998 | Allen et al. | |
| 5,838,429 A | 11/1998 | Hahn | |
| 5,846,835 A | 12/1998 | Sisbarro et al. | |
| 5,945,345 A | 8/1999 | Blatt et al. | |
| 5,968,839 A | 10/1999 | Blatt et al. | |
| 5,995,236 A | 11/1999 | Roth et al. | |
| 6,009,632 A * | 1/2000 | Douglas | 33/562 |
| 6,027,692 A | 2/2000 | Galen et al. | |
| 6,046,057 A | 4/2000 | Nazareth et al. | |
| 6,055,060 A | 4/2000 | Bolduan et al. | |
| 6,100,966 A | 8/2000 | Kreuwel | |
| 6,156,271 A | 12/2000 | May | |
| 6,187,269 B1 | 2/2001 | Lancesseur et al. | |
| 6,201,607 B1 * | 3/2001 | Roth et al. | 356/445 |
| 6,234,974 B1 | 5/2001 | Catt et al. | |
| 6,277,650 B1 | 8/2001 | Nazareth et al. | |
| 6,285,454 B1 | 9/2001 | Douglas et al. | |
| 6,319,676 B1 | 11/2001 | Nazareth et al. | |
| 6,335,203 B1 | 1/2002 | Patel et al. | |
| 6,372,514 B1 | 4/2002 | Lee | |
| 6,565,503 B2 | 5/2003 | Leysieffer et al. | |
| 6,602,702 B1 | 8/2003 | McDevitt et al. | |

(Continued)

OTHER PUBLICATIONS

Clearblue Easy Digital Pregnancy Testing System Brochure; Unipath Diagnostics Inc.; Waltham, MA.

*Primary Examiner* — Ann Lam
(74) *Attorney, Agent, or Firm* — Knobbe, Martens, Olson & Bear, LLP

(57) ABSTRACT

The invention is an electronically processed single-step test device for detecting the presence of a preselected analyte in a fluid. The device includes a hollow rectangular outer casing, disposed within co-joined upper and lower sections of the casing are assay material, an electronic processing system, and a LCD display. The LCD display is observable through a viewing window. The assay material is a sorptive material including a fluid sample application region in the form of a sample wick in fluid communication with a test strip. The test strip includes an analyte capture region adjacent to a light shield. The electronic processing system includes red and green LEDs which are alternately pulsed or energized over predetermined periods of time to determine if fluid test results show a marker or markers in the capture region indicative of the presence of a preselected analyte in the fluid. If so, Yes+ is displayed on the LCD. If not, No– is displayed on the LCD.

13 Claims, 34 Drawing Sheets

(56) References Cited

U.S. PATENT DOCUMENTS

| | | |
|---|---|---|
| 6,867,051 B1 * | 3/2005 | Anderson et al. ............. 436/518 |
| 6,906,802 B2 * | 6/2005 | Voelkel ......................... 356/446 |
| 7,220,597 B2 | 5/2007 | Zin et al. |
| 7,239,394 B2 * | 7/2007 | Sharrock et al. ............. 356/436 |
| 7,262,857 B2 * | 8/2007 | Koike ........................... 356/445 |
| 7,270,970 B2 * | 9/2007 | Anderson et al. ............ 435/7.94 |
| 7,317,532 B2 * | 1/2008 | Sharrock et al. ............. 356/436 |
| 7,763,454 B2 * | 7/2010 | Nazareth et al. ............ 435/287.7 |
| 8,303,518 B2 | 11/2012 | Aceti et al. |
| 2003/0119202 A1 | 6/2003 | Kaylor et al. |
| 2003/0207466 A1 | 11/2003 | Po Lee |
| 2003/0211634 A1 | 11/2003 | Jerome et al. |
| 2003/0219908 A1 | 11/2003 | Davis et al. |
| 2005/0036148 A1 * | 2/2005 | Phelan ......................... 356/446 |
| 2005/0130293 A1 * | 6/2005 | Blatt et al. ................. 435/287.2 |
| 2006/0148096 A1 | 7/2006 | Jina |

\* cited by examiner

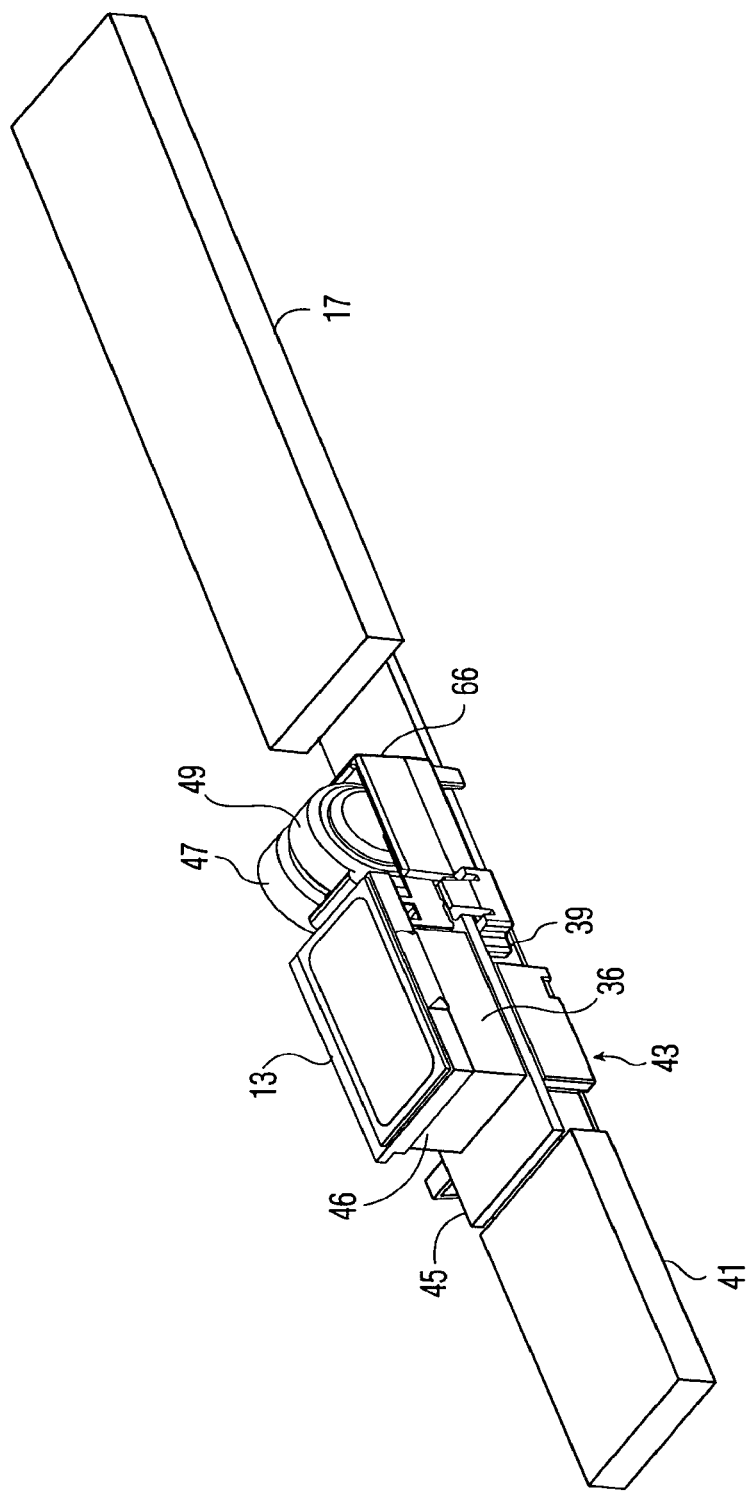

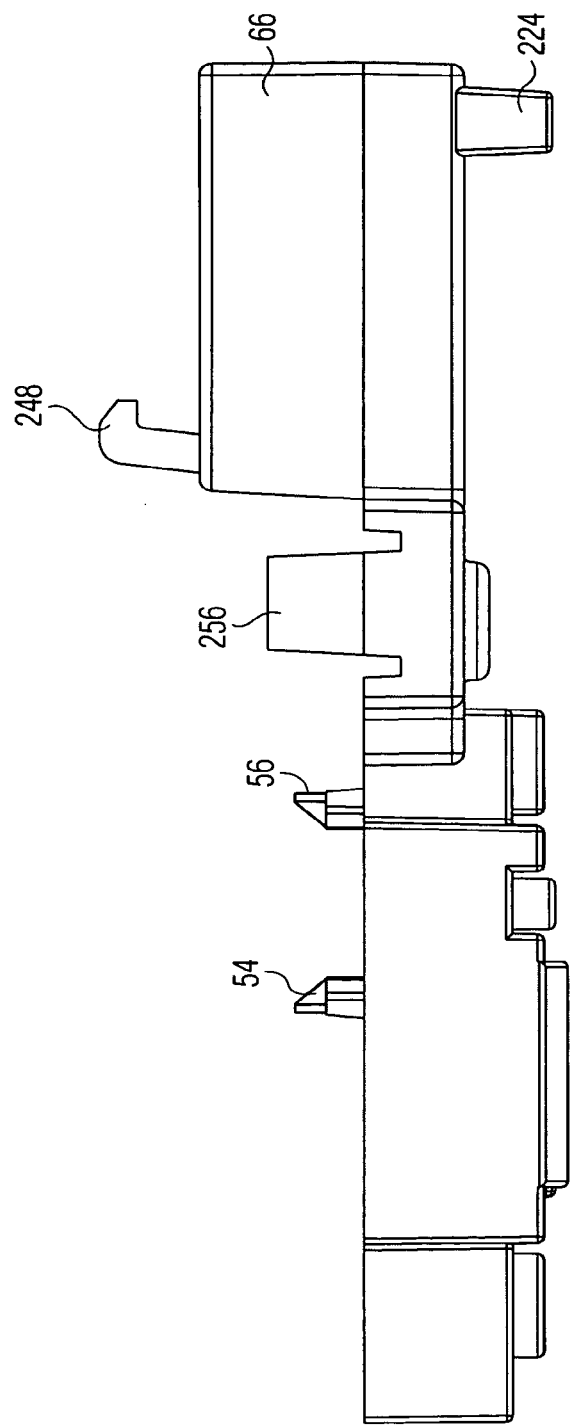

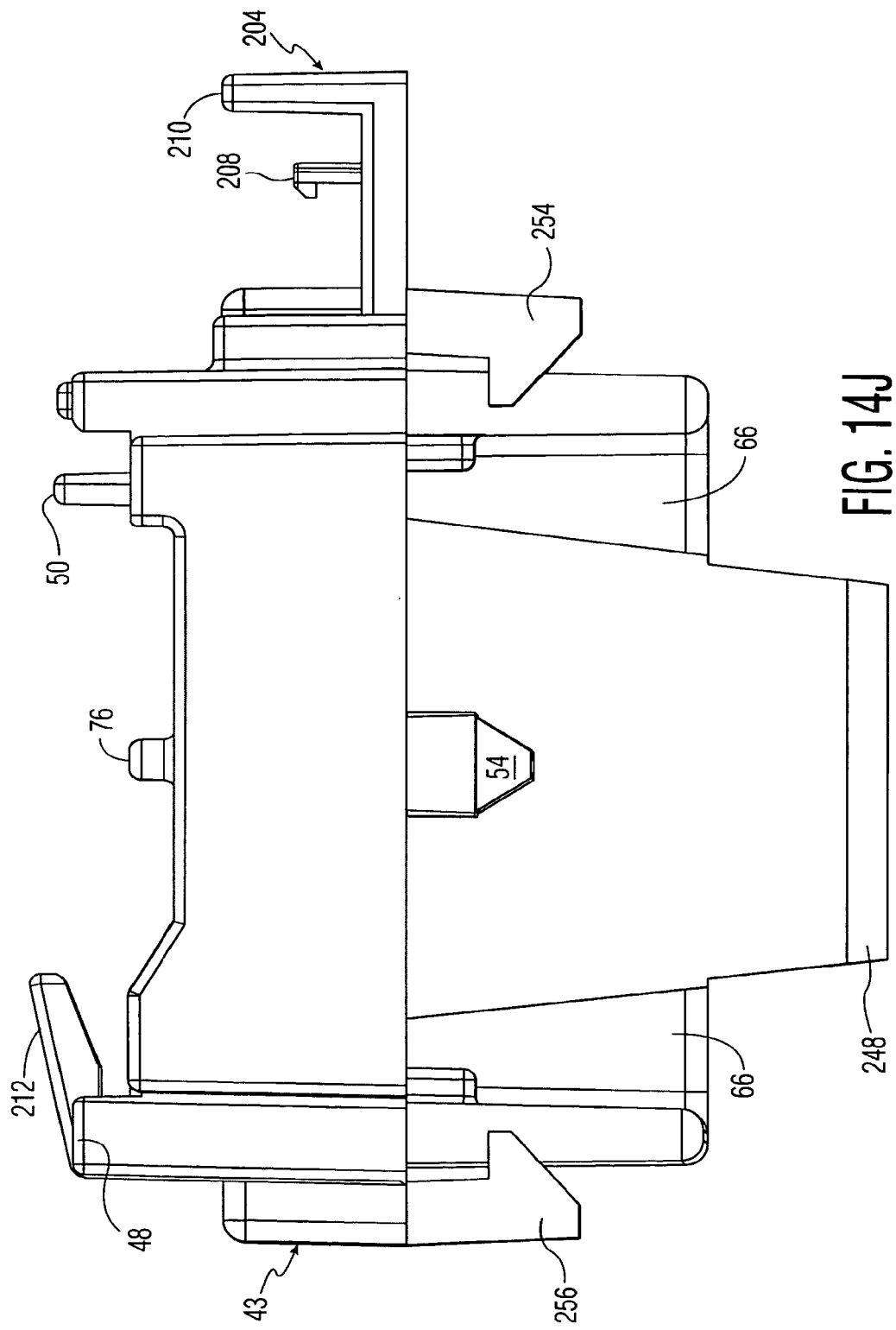

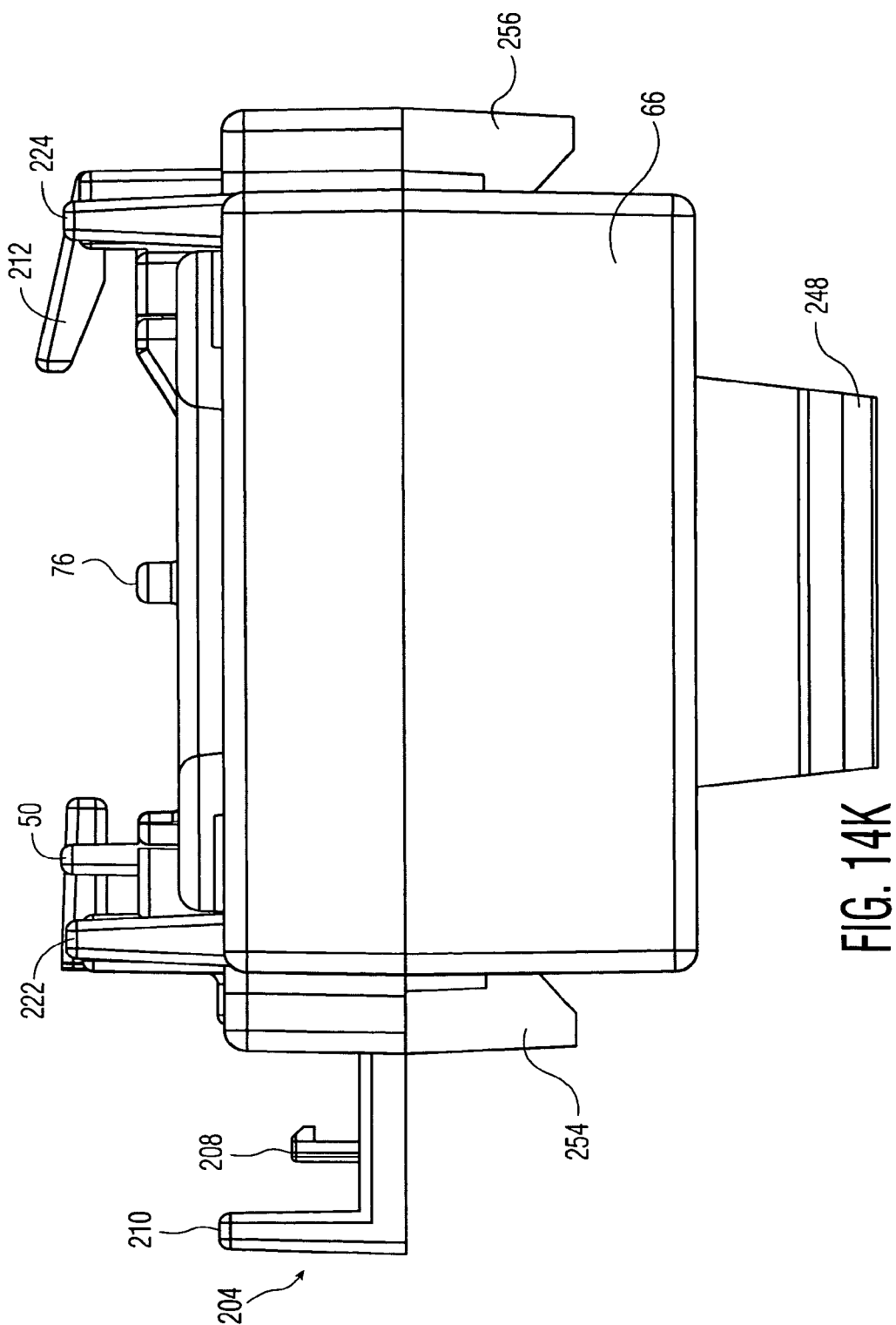

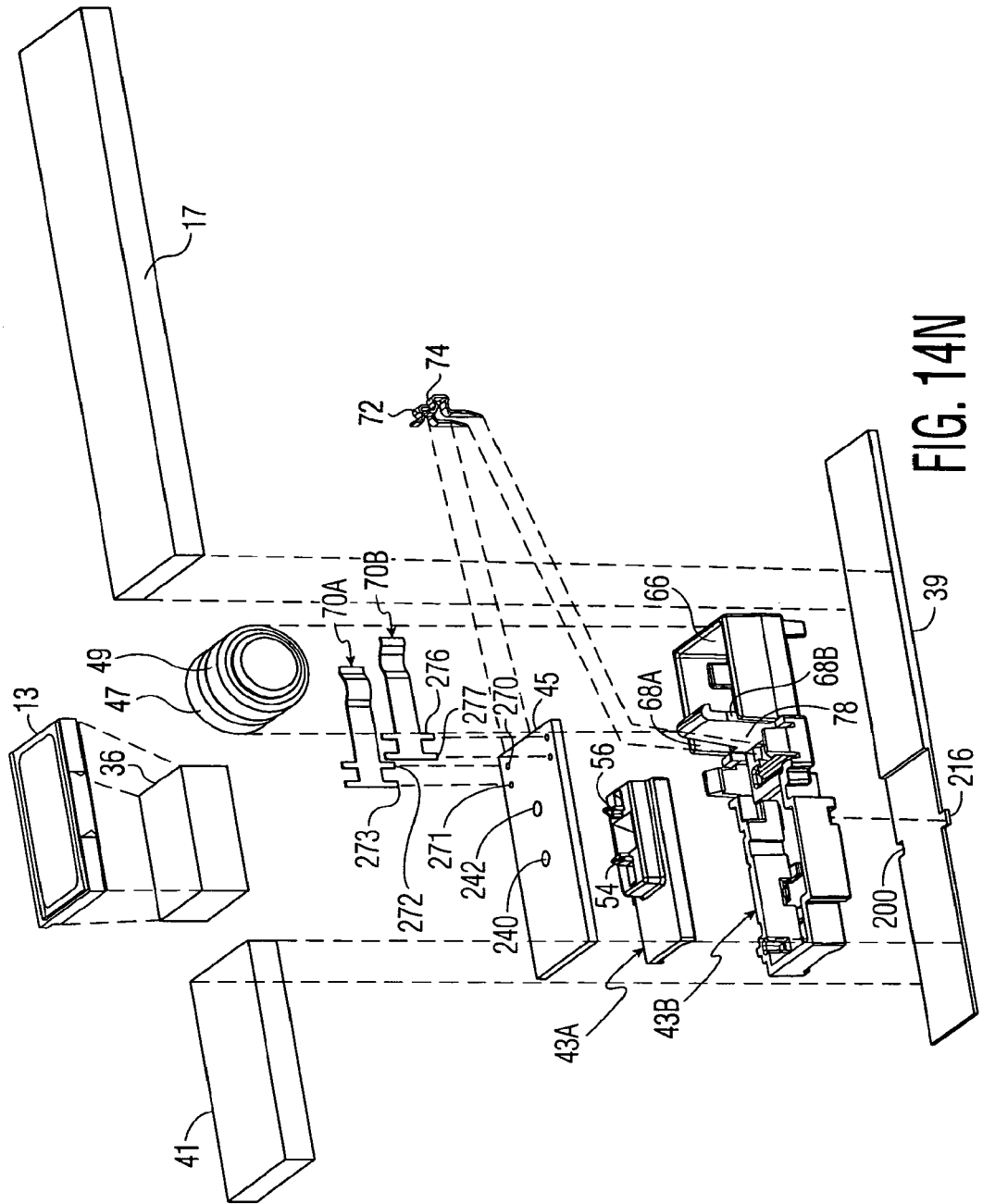

ELECTRONIC ANALYTE ASSAYING DEVICE

RELATED APPLICATIONS AND PATENTS

The present invention is related to U.S. Pat. No. 5,739,041, entitled "IMPROVED DIAGNOSTIC DETECTION DEVICE"; and to U.S. Pat. No. 6,319,676, entitled "DIAGNOSTIC DEVICE AND METHOD"; and to U.S. Pat. No. 5,846,835, entitled "MANUFACTURING METHOD FOR LAMINATED IMMUNODIAGNOSTIC TEST DEVICE"; and to Design U.S. Pat. No. Des. 390,667, entitled "DIAGNOSTIC DETECTION DEVICE"; and to U.S. Pat. No. 6,046,057, entitled "ANALYTE ASSAYING DEVICE"; and to U.S. Pat. No. 6,277,650, entitled "ANALYTE ASSAYING DEVICE"; and to Design application Ser. No. 29/174,065, entitled ELECTRONIC DIAGNOSTIC DETECTION DEVICE CASING WITH REMOVABLE CAP, filed Jan. 10, 2003; all of which are incorporated herein in their entirety to the extent that they do not conflict herewith. These related applications and patents are all assigned to the same Assignee as the present invention.

FIELD OF THE INVENTION

This invention relates to an improved device for assaying a preselected analyte, such as an antigen, in a body fluid, such as urine, and more particularly relates to such a device including electronic interpretation of the read area in a lateral flow strip, for electronically providing a display of the results of the interpretation.

BACKGROUND OF THE INVENTION

A variety of ligand-receptor assays have been developed to detect the presence of a preselected analyte in body fluid. Typically, these assays involve antibody-antigen interactions, synthetic conjugates comprising radioactively, enzymatically, spectroscopically, or visually observable tags, and specially designed reactor chambers. In most assays, there is a receptor (e.g., an antibody) that is specific for the preselected analyte (e.g., an antigen), and a means for detecting the presence and/or amount of a resulting receptor-analyte (e.g., antibody-antigen) complex. Most current assays are designed to make a quantitative determination, but in many circumstances all that is required is a qualitative result, i.e., a positive or negative signal. Examples of such qualitative assays include, for example, pregnancy tests, ovulation tests as well as a variety of other types of urine analysis. In these tests, visually observable signals such as the presence of agglutination of a color change are preferred.

The assays optimally are performed using single-step devices wherein the only step the user need perform prior to observation of the result is application of the sample to be assayed onto the device. Single-step devices, therefore, obviate the necessity of performing, subsequent to the application of the sample, a series of manipulations which may be time consuming and/or may introduce errors in the end result. Accordingly, several single-step devices, for example those described in International Application Nos. WO 88/08534, published Nov. 3, 1988, have been developed and are commercially available.

The single-step device described in International Application Published No. WO 88/08534 comprises a hollow casing containing a porous assay material communicating with the exterior of the casing via a fluid sample receiving member. During operation, the user applies the fluid test sample onto the fluid sample receiving member protruding out of the casing. Thereafter, the fluid sample while traversing the carrier material enters the casing and moves to a capture region disposed upon the carrier material. The capture region comprises a means for binding a preselected analyte. When the fluid sample reaches the capture region, assuming that the fluid sample contains the analyte, the analyte binds to the capture region. The bound analyte subsequently can be visualized within the capture region.

It has been found, however, that invalid test results may arise from the use of single-step devices, particularly devices wherein the fluid sample is applied directly from a fluid stream through a urine inlet port defined by the casing onto assay material enclosed therein.

An improved single-step test device for detecting the presence of a preselected analyte in an urine stream is described in the above-cited U.S. Pat. Nos. 6,046,057 and 6,277,650. The device includes a hollow rectangular outer casing and an assay material disposed within co-joined upper and lower sections of the casing. The outer casing includes a urine inlet port; a viewing window in the upper section; at least the upper section consisting of transparent material; and may also include at least one drainage vent spaced about the urine inlet port. The assay material is a sorptive material including: a urine sample application region adjacent to, and in fluid communication with the urine inlet port; a capture region adjacent to the viewing window; and a fluid flow path for transporting a liquid sample between the urine sample application region and the analyte capture region. The flow of urine in the fluid path is observable through the transparent upper section for confirming a test is operative. The drainage vent is located to permit excess urine entering the casing from the urine stream to exit the casing thereby to minimize hydraulic pressure induced flooding of the assay material disposed within the casing and to reduce the frequency of false test results. In this improved device, a colloidal gold label antibody reagent is deposited on a release region of assay material. When, in this example, urine is applied to the sample absorbent material 8, the urine moves by capillary action or sorbent movement downstream toward window. When the urine contacts the reagent, it reconstitutes the reagent material, causing the reagent to move with the urine front along the flow path. When the reconstituted marker reagent passes through the window region 11, capture means are included in the capture region 85 to cause a single colored line to appear indicative of no pregnancy, or a double line to appear indicative of pregnancy. Although this device represented a very positive improvement over the prior single-step test devices, a user must interpret the lines that appear in the associated window to determine whether or not the test result is indicative of pregnancy. The present inventors recognized that if the requirement for a user to have to interpret between single colored lines and double lines can be eliminated, whereby a simple display of the word Yes+ for pregnancy, or No− for non-pregnancy, could be provided in a further improved such device, mistakes in interpretation by a user can be substantially eliminated. Note that as previously indicated above, the aforesaid two patents, and the present invention, are all commonly owned.

SUMMARY OF THE INVENTION

Accordingly, with the problems in the prior art in mind, it is an object of the present invention to provide both an improved single-step detection device for reliably detecting the presence of a preselected analyte within a body fluid, when the body fluid, an example being urine, is applied directly from a fluid stream, a urine stream for example, onto assay material disposed within the device, and to provide electronic interpretation of the test results for displaying in a window Yes+ as being indicative of pregnancy, or No– indicative of non pregnancy, for example.

It is another object of the invention to provide a method for detecting a preselected analyte using a single-step device including electronic interpretation as described herein.

It is yet another object of the invention to provide a method for producing a single-step detection device including electronic or electro-optical means for interpreting and displaying test results, as described herein.

Yet another object of the invention is to provide a method and apparatus for permitting a user, after applying a fluid sample onto assay material, to shortly thereafter view the test results in a window consisting of the word Yes+ being displayed indicative of pregnancy, or the word No– being displayed indicative of non pregnancy, for example.

One embodiment, the present invention provides a device having an outer casing enclosing an assay material, and electro-optical system means, for detecting the presence of an analyte in a urine stream. The assay material defines a capture region for binding the analyte. The outer casing includes a removable cap for exposing a portion of a sample wick to which urine is applied directly from a urine stream, whereafter the cap can be reinstalled. The urine flows from the sample wick onto a test strip containing assaying material. The electro-optical means monitors the overall operation of the device in the capture region for interpreting the test results, and for displaying the results on a small display screen located in a viewing window. The electro-optical means includes electronic processing means for interpreting changes in color in the capture region, such as a test result producing two lines indicative of pregnancy, or one line indicative of non-pregnancy, whereby the processing means displays Yes+ on the display for pregnancy, and No– for non pregnancy, for example. In one embodiment of the present invention, the display is a liquid crystal display (LCD).

BRIEF DESCRIPTION OF THE DRAWINGS

The present invention will now be more particularly described with reference to the accompanying drawings, in which like items are identified by the same reference designation, wherein:

FIG. 14A is a perspective view of the assembly of a sample wick, test strip, printed circuit board with electronic circuitry or components installed, light shield, batteries, LCD display, and absorber material;

FIG. 14H is a left side elevational view of the light shield;

FIG. 14J is a front elevational view of the light shield;

FIG. 14K is a back elevational view of the light shield;

FIG. 14N is an exploded assembly view of the assembly of FIG. 14A;

DETAILED DESCRIPTION OF THE INVENTION

Figure 1:
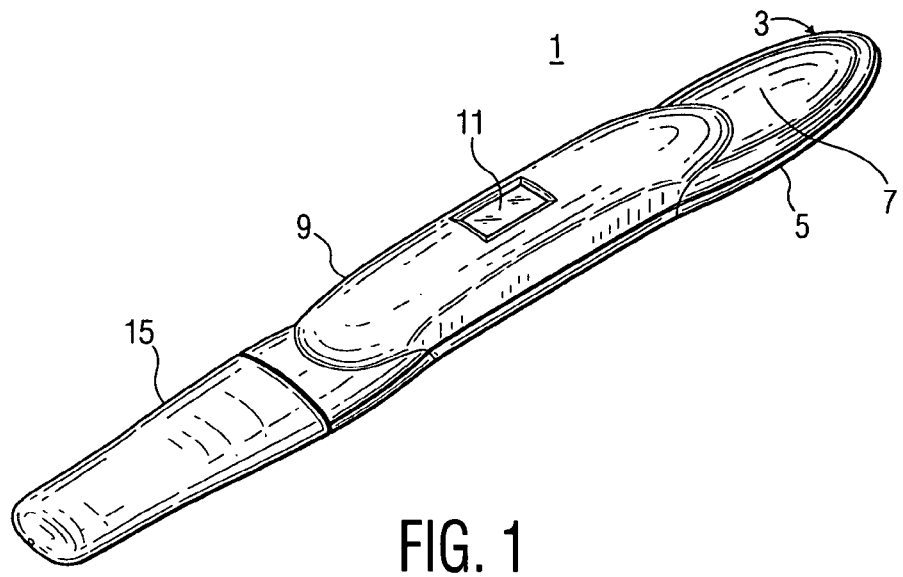
FIG. 1 is a perspective view looking toward the top and left side of the casing of the present device for one embodiment of the invention.
Figure 2:
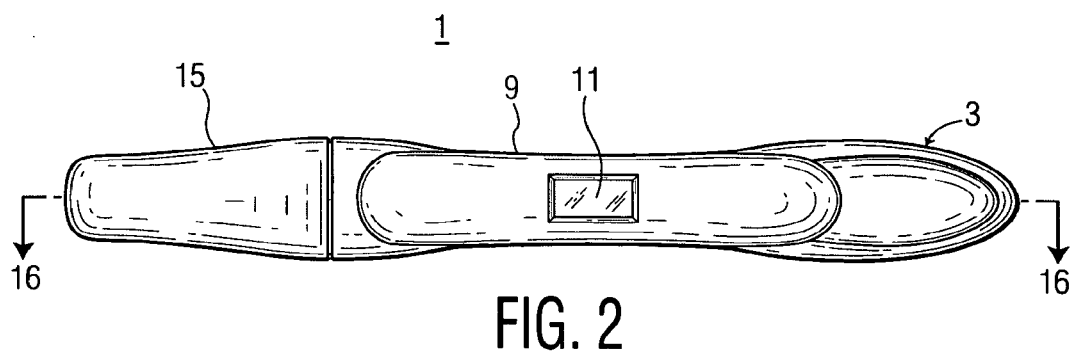
FIG. 2 is a top plan view of the casing of FIG. 1.

The present invention provides electro-optical processing in an improved single-step device for detecting a preselected analyte in a urine stream. With reference to FIGS. 1 through 7, in one embodiment of the present invention, the device 1 includes a casing 3 that has a front portion 5 configured to provide a top recessed portion 7 shaped to permit a user to place their thumb into the recessed portion 7 and their forefinger on the bottom of the front portion 5 to securely hold the device 1. A raised more central portion 9 of the case 3 includes a centrally located window 11 to permit a user to observe test results provided on an underlying LCD display 13 (see FIG. 8). A removable cap 15 is provided at the other end of the device 1. In one embodiment, the device 1 with the cap 15 installed on the casing 3 is about 5.7 inches long, the cap 15 being about 1.5 inches long. The central portion 9 of casing 3 is about 1.5 inches long, in this example. The dimensions are not meant to be limiting, and are given for purposes of illustration only.

Figure 7:
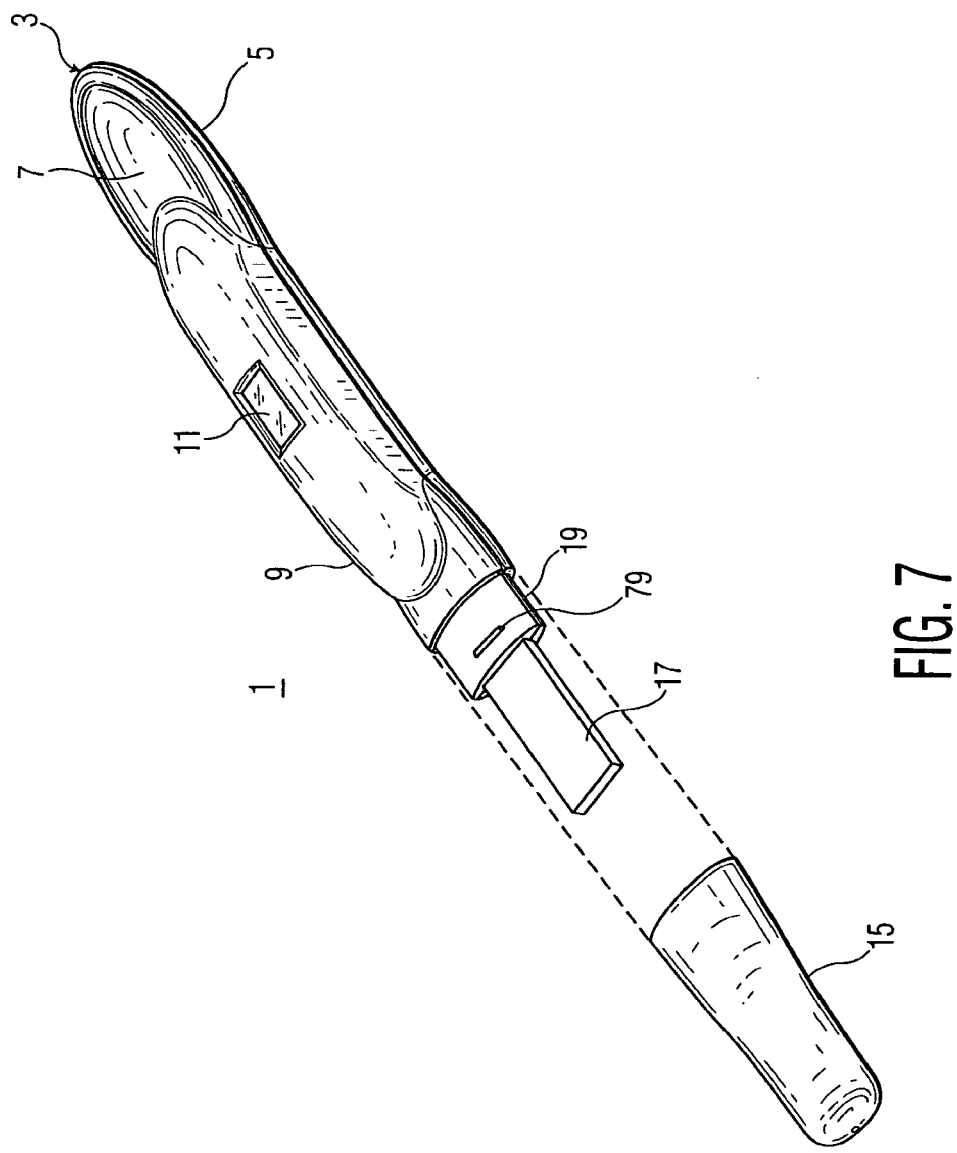
FIG. 7 is a perspective view of the device looking toward the top and lefthand side with the cap removed, as shown in an exploded assembly view.

As will be described in greater detail below, the device 1 is battery powered, disposable, and extremely easy to use. More specifically, to use the device a user merely has to remove the cap 15 to expose a sample wick 17, as shown in FIG. 7. Next, the user inserts the sample wick into a urine stream for wetting the wick 17 with the urine. The cap 15 can then be replaced or reinstalled, and the user merely waits for a message to be shown on the LCD display 13 through the window 11 of case 3. In one embodiment of the invention, from the time that the sample wick 17 is wetted with urine, it takes only about three minutes for the device 1 to complete the test and provide the results on the LCD display 13. As previously indicated, if the user is pregnant, a Yes+ message will appear on display 13, and if not pregnant the message No− will appear, in this example.

Figure 3:
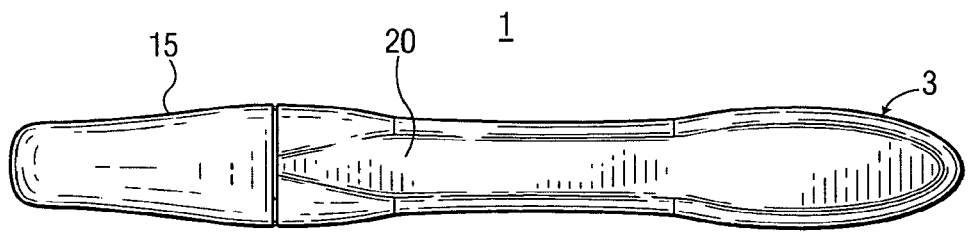
FIG. 3 is a bottom plan view of the casing of FIG. 1.
Figure 4:
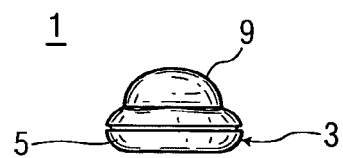
FIG. 4 is a front elevational view thereof.
Figure 5:
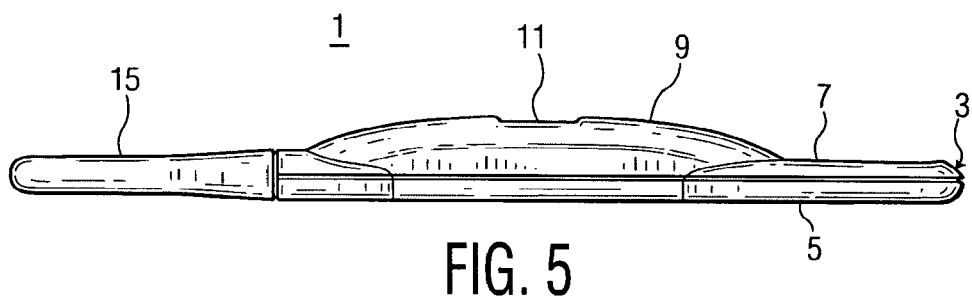
FIG. 5 is a left side elevational view thereof, the right side elevational view being a mirror image thereof.
Figure 6:
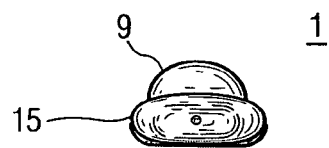
FIG. 6 is a back elevational view thereof.

The bottom 20 of device 1 is substantially flat as shown in FIGS. 3 and 5. Also, note that a portion of the sample wick 17 provided to a user extends from a reduced portion 19 of case 3, with the reduced portion 19 also being configured to receive the cap 15 (see FIG. 7).

Figure 8:
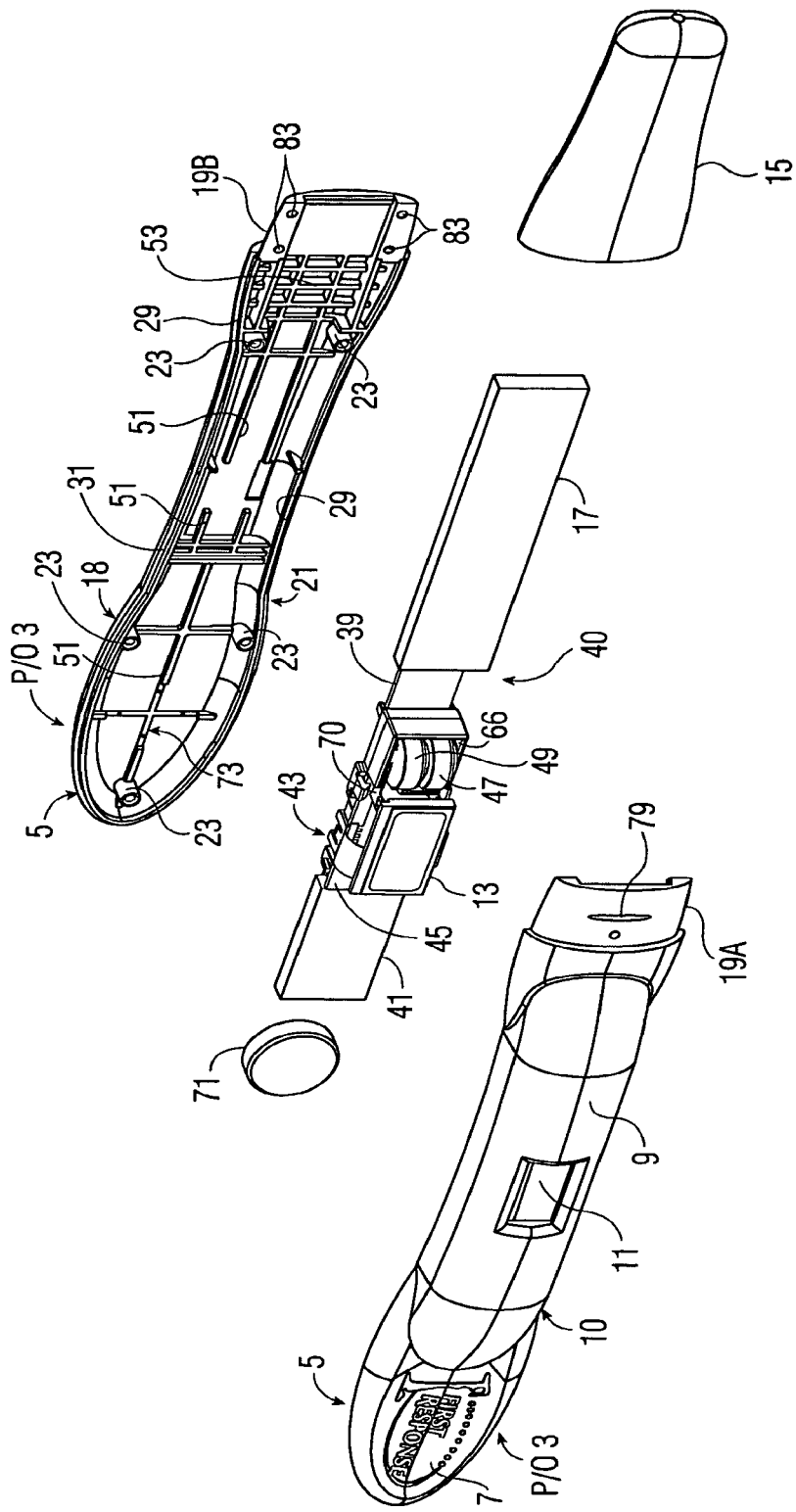
FIG. 8 is a exploded assembly view of the device for one embodiment of the invention.
Figure 9:
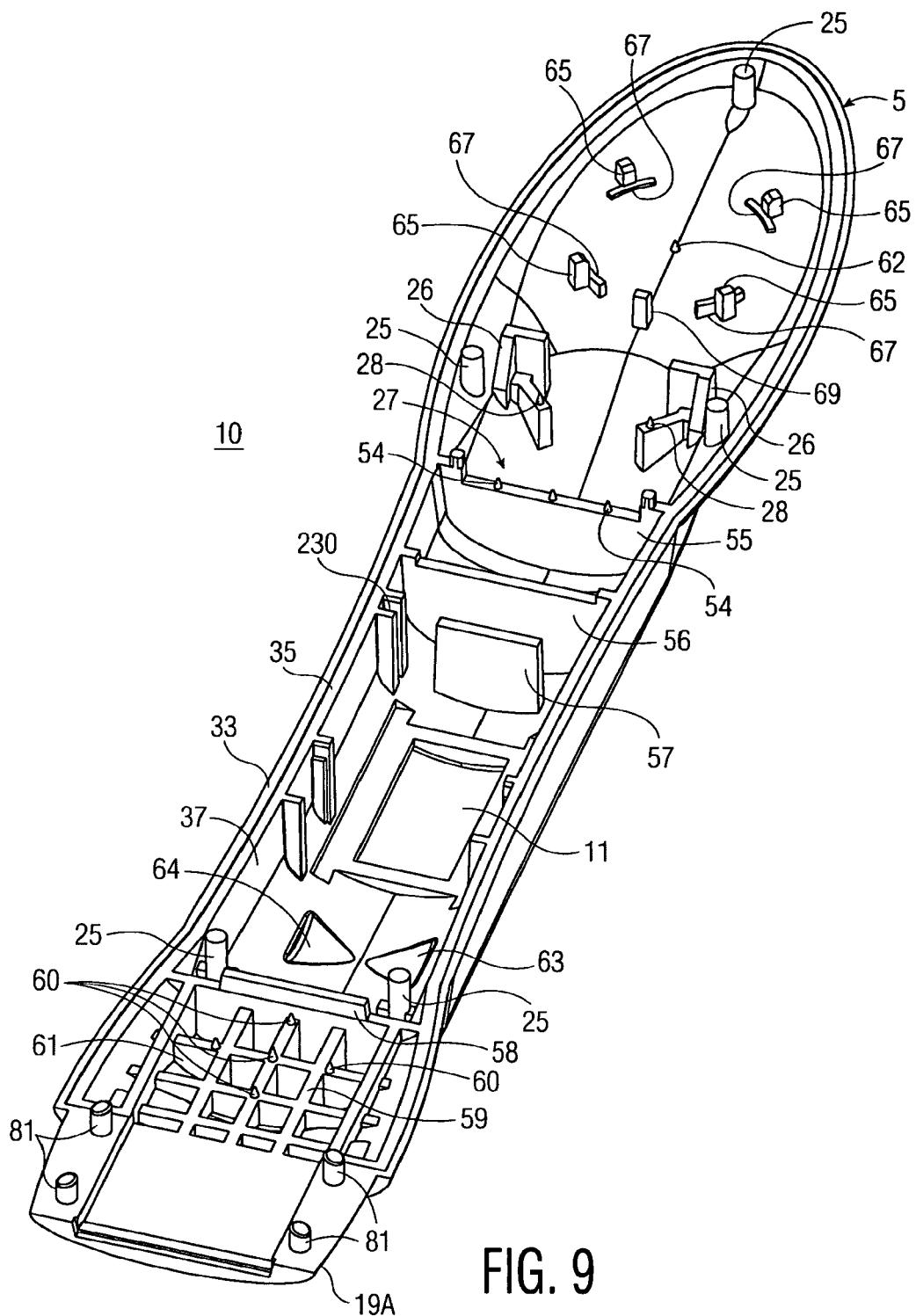
FIG. 9 is a perspective view showing the interior casing design for the top half portion thereof for one embodiment of the invention.

An exploded assembly view of one embodiment of the present device is shown in FIG. 8. The interior configuration 21 of the bottom half portion 18 of the casing 3 includes a plurality of standoff sockets 23 for receiving a plurality of standoff pins 25, respectively, located in the interior portion 27 of the top half 10 of the casing 3, as shown in FIG. 9. Also, the interior portion 21 of the bottom half 18 includes a circumferential lip 29 protruding outward from a ledge portion 31 (see FIGS. 8 and 10). With further reference to FIG. 9, the interior portion 27 of the top half section 10 includes a circumferential ledge 33 that extends beyond or higher than a top edge 35 of an interior wall 37. When the top and bottom half sections 10, 18 respectively, are joined together, the sockets 23 of the bottom half section 18 securely retain associated pins 25 of the top half section 10, and the protruding circumferential lip 29 of the bottom half section has its top edge abutted against the top edge 35 of interior wall 37 of the top half section 10, with the lip 29 of the bottom half section 18 proximate against the edge of the protruding lip 33 of the top half section 10, the two half sections 10, 18 of casing 3 can be permanently secured together after assembly of the device through electrode welding, or use of an appropriate adhesive material.

Figure 14B:
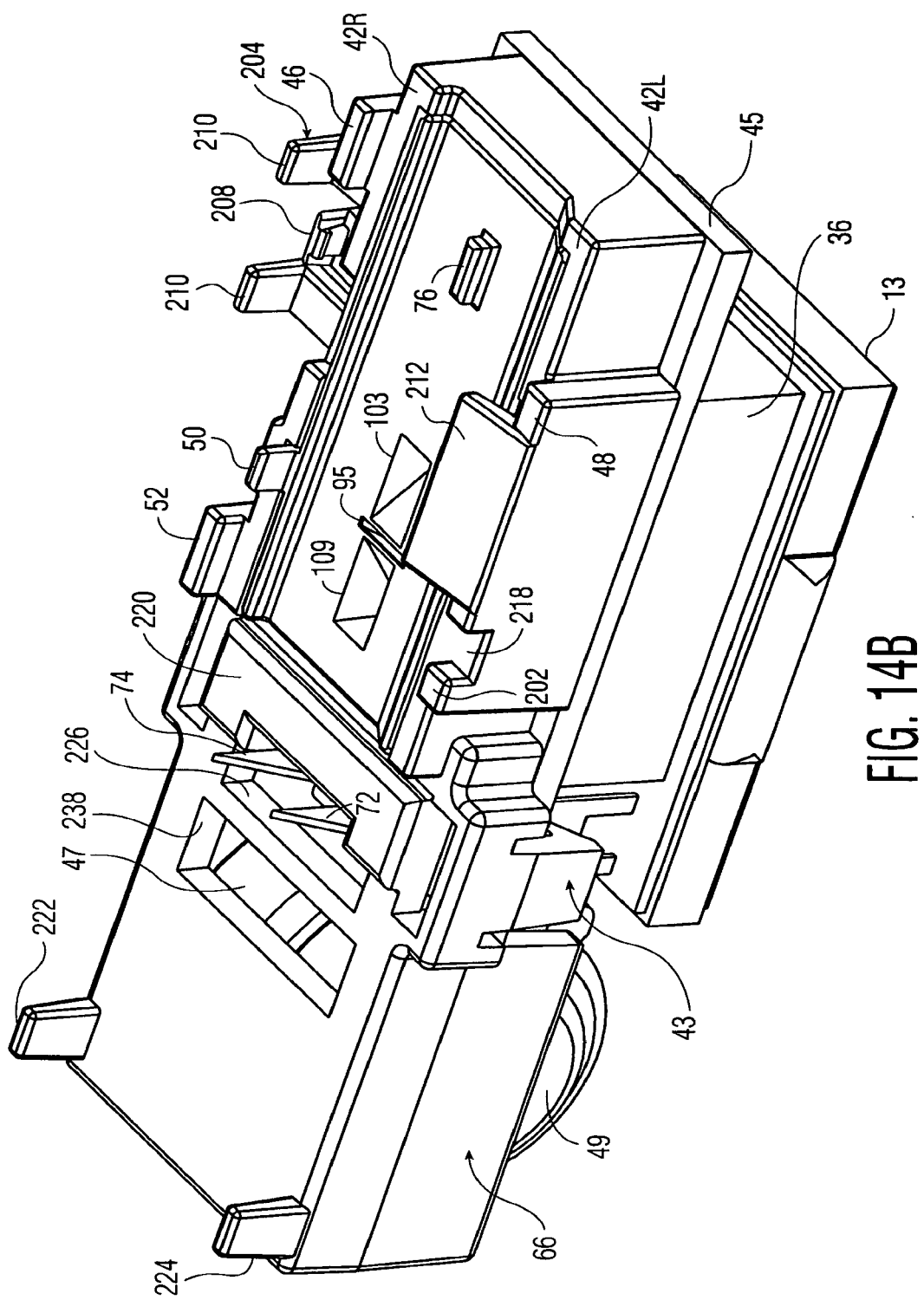
FIG. 14B is an enlarged partial perspective view looking toward the bottom and left side of the light shied in an assembly including a portion of the printed circuit board, the battery, and the LCD display.
Figure 14C:
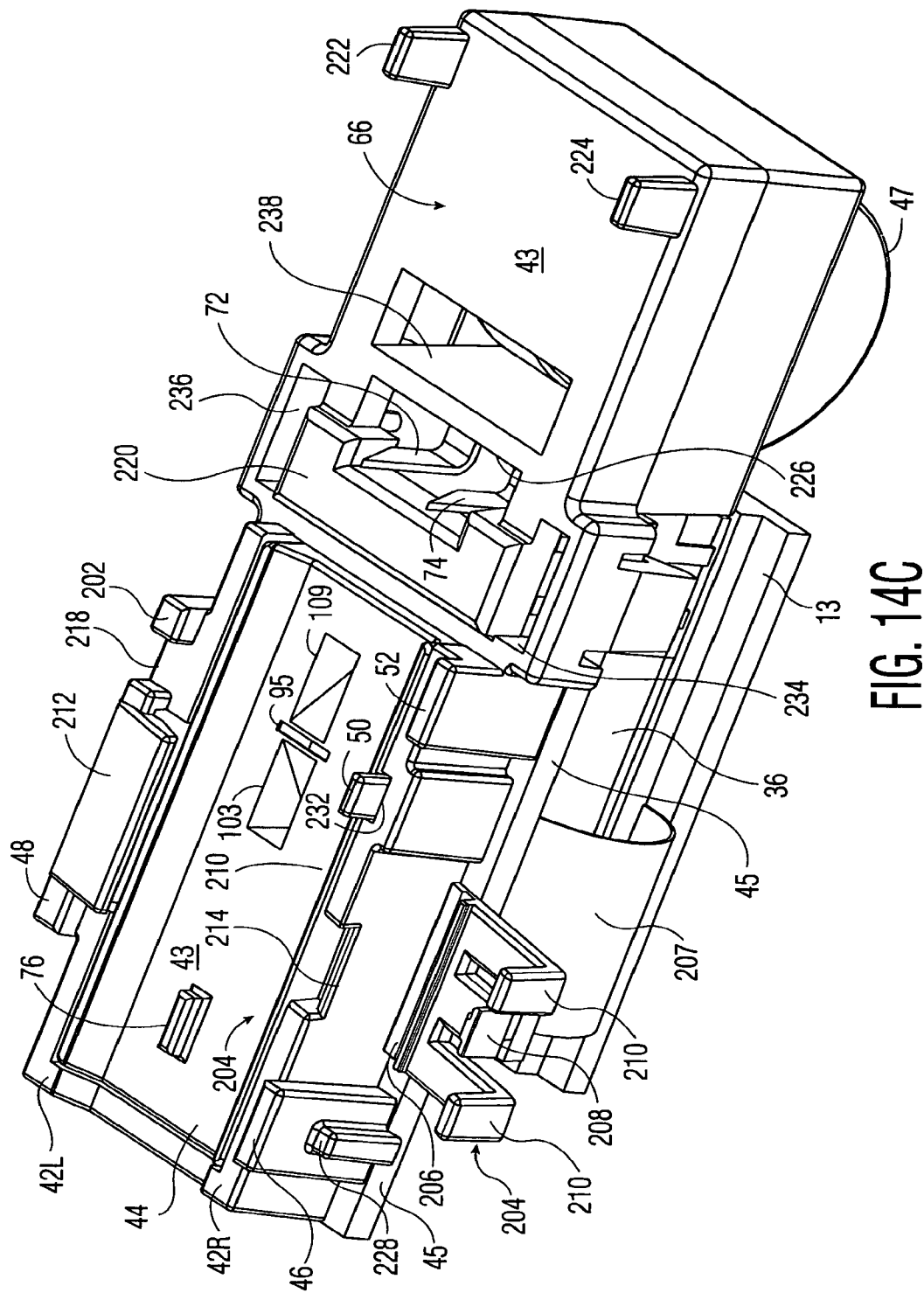
FIG. 14C is a perspective view looking toward the bottom and right side of the light shield.
Figure 14D:
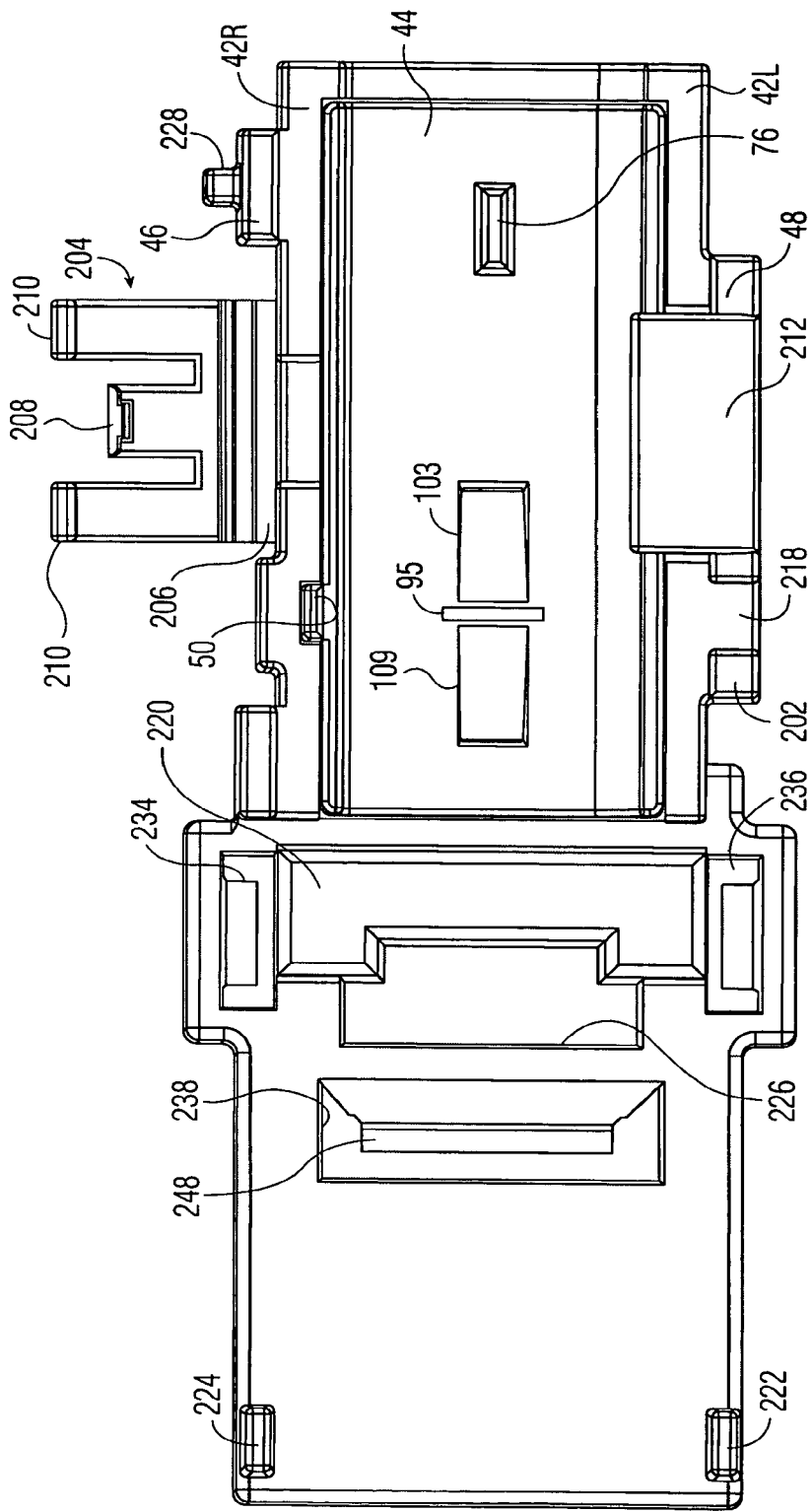
FIG. 14D is a bottom plan view of the light shield.
Figure 14E:
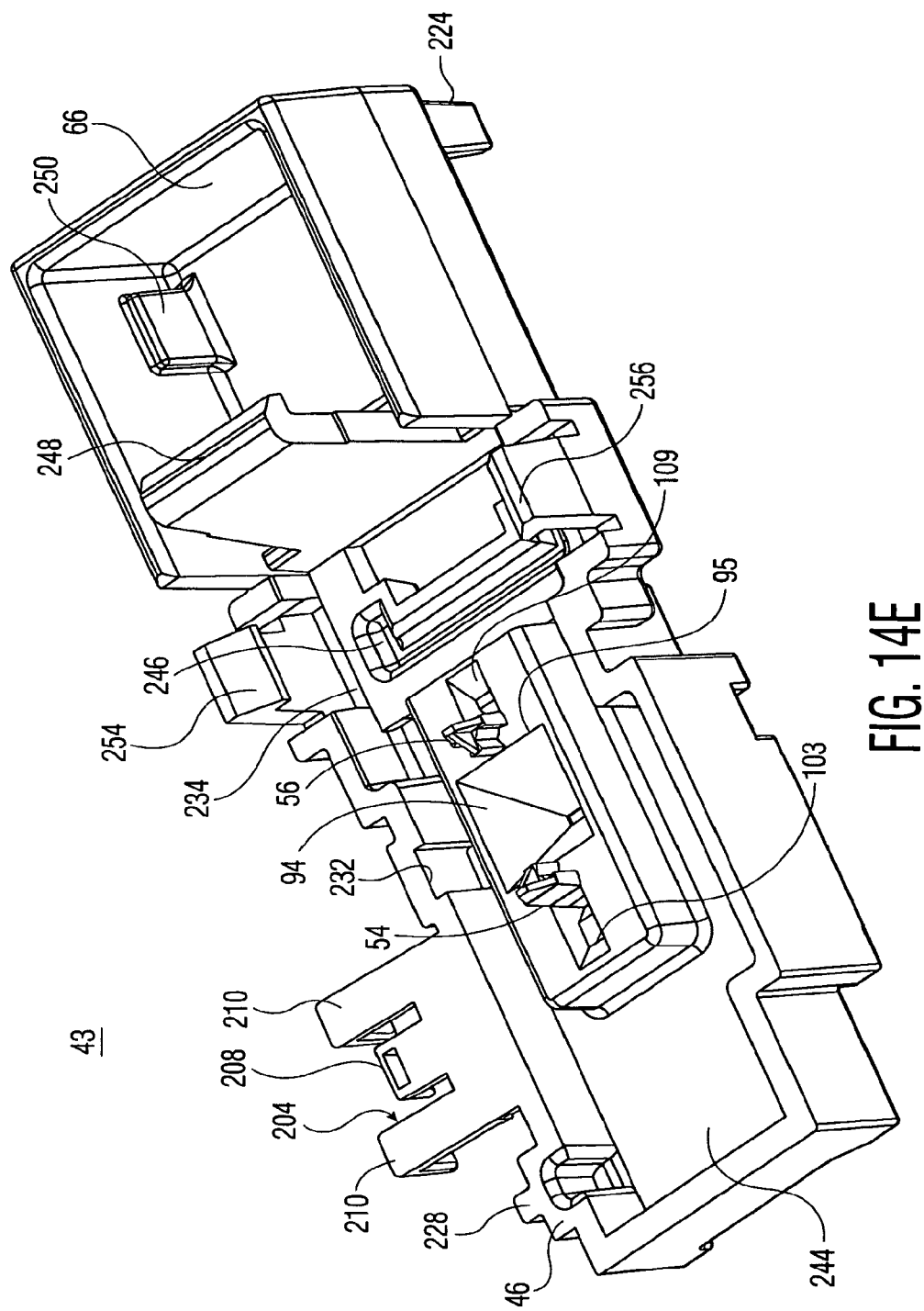
FIG. 14E is a perspective view looking toward the top and right side of the light shield.
Figure 14F:
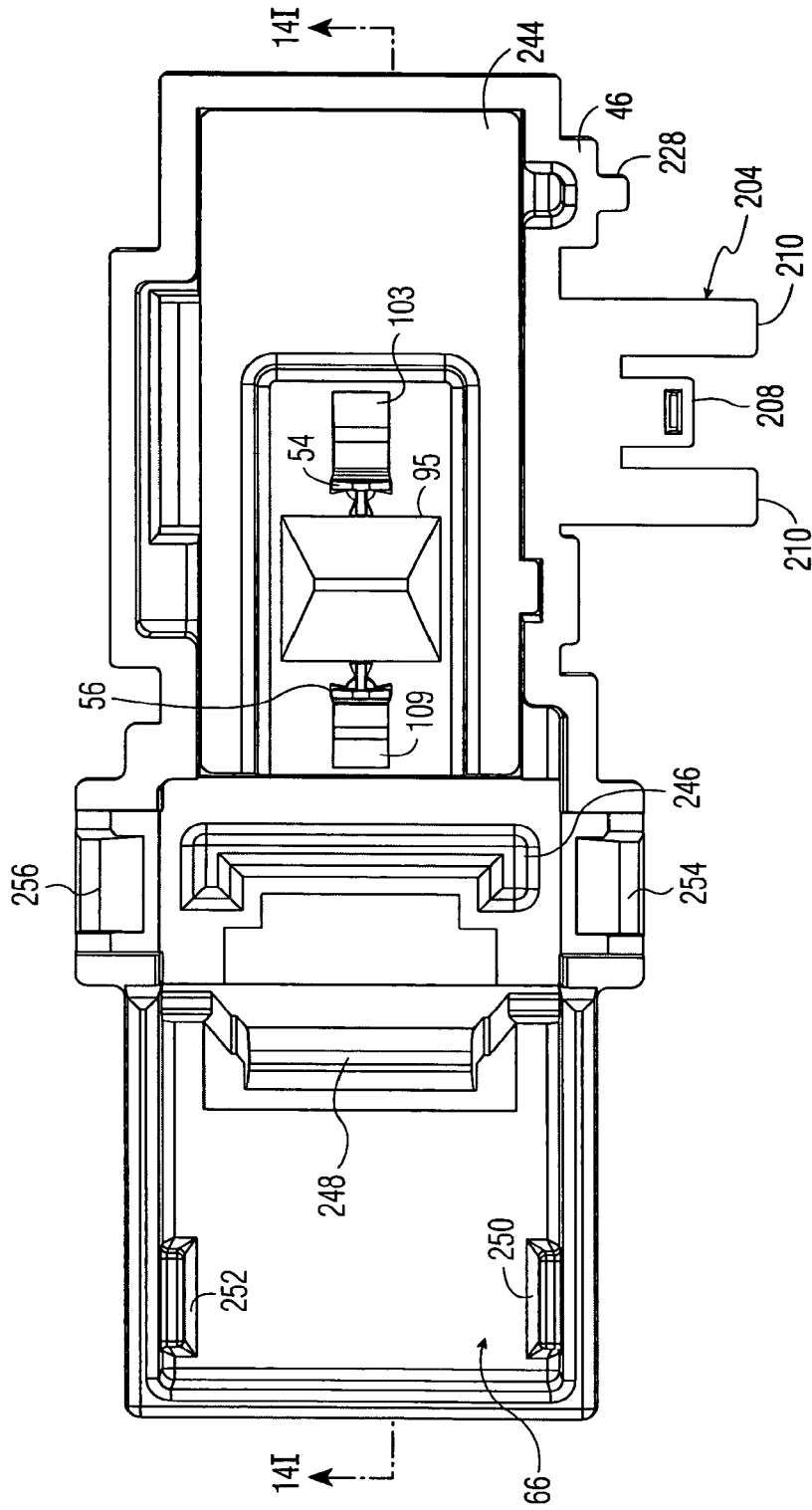
FIG. 14F is a top plan view of the light shield.
Figure 14G:
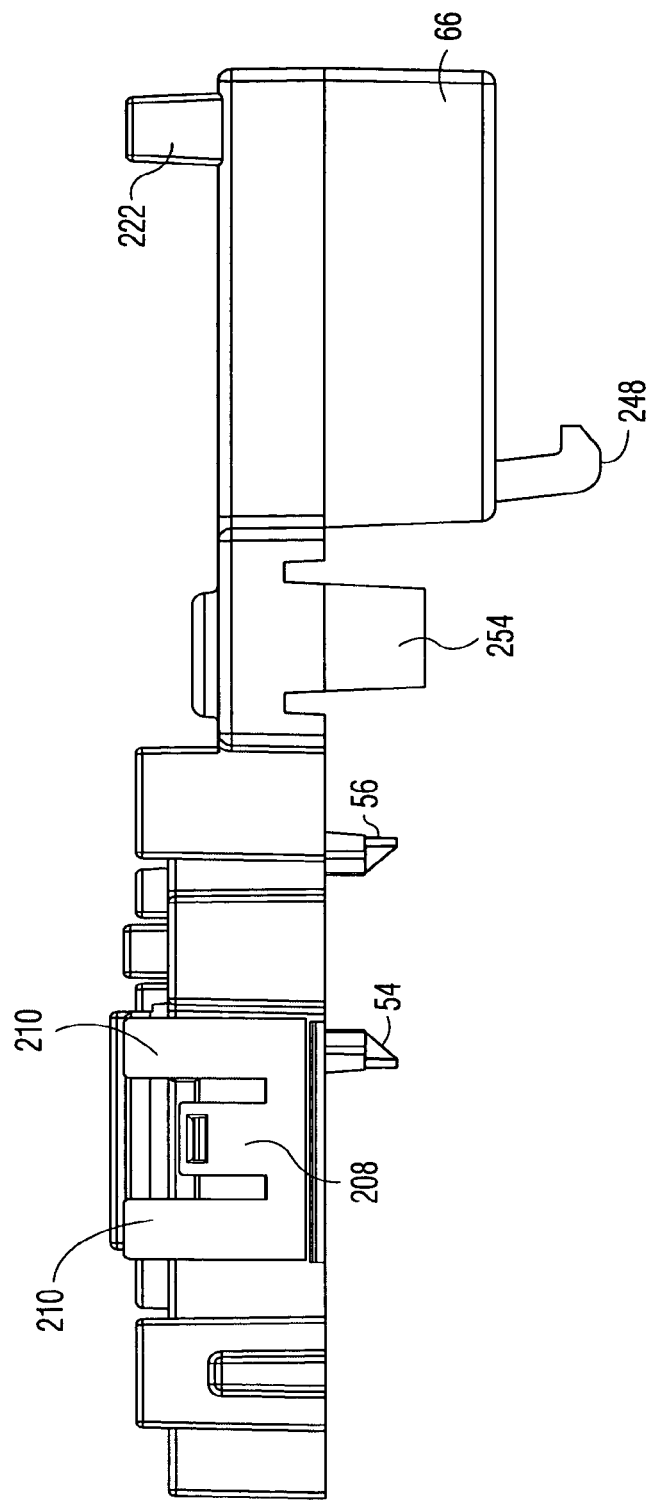
FIG. 14G is a right side elevational view of the light shield.
Figure 14I:
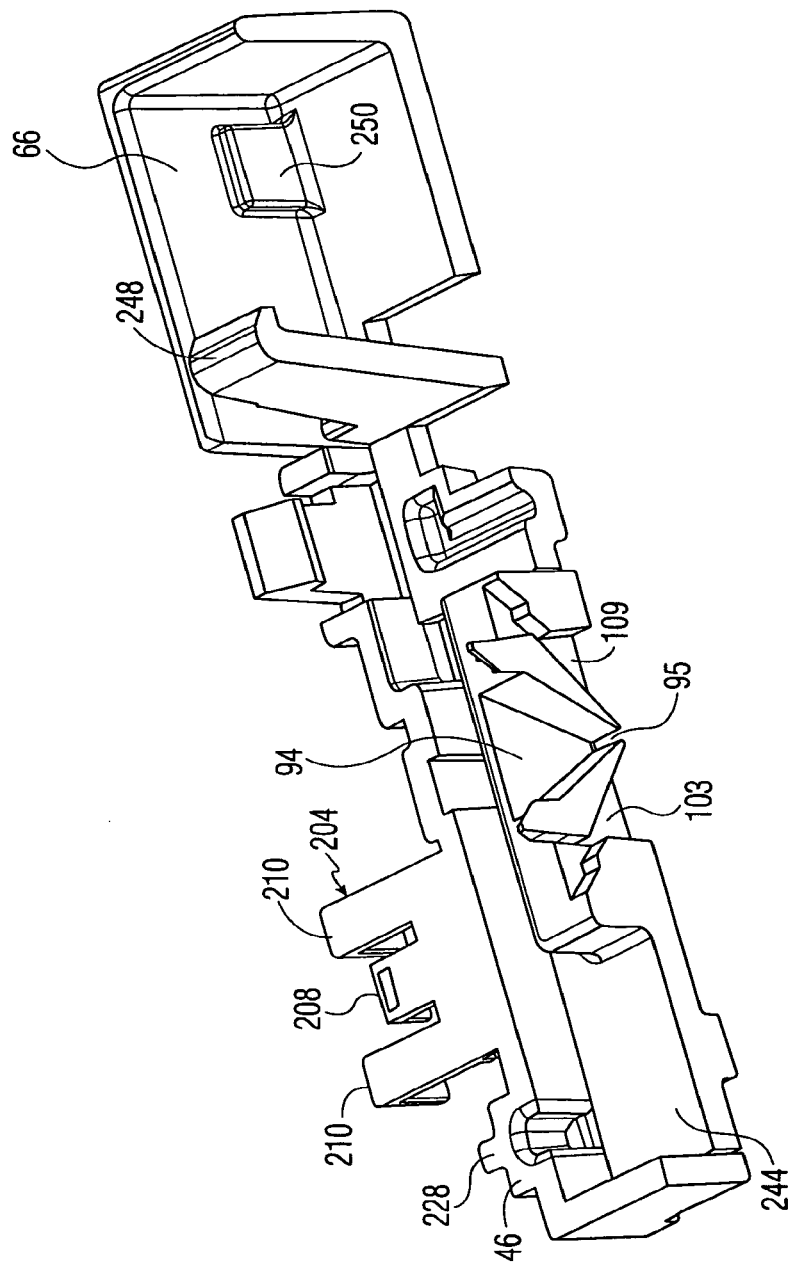
FIG. 14I is a cross sectional perspective view taken along 14I-14I of FIG. 14F of the light shield.
Figure 14L:
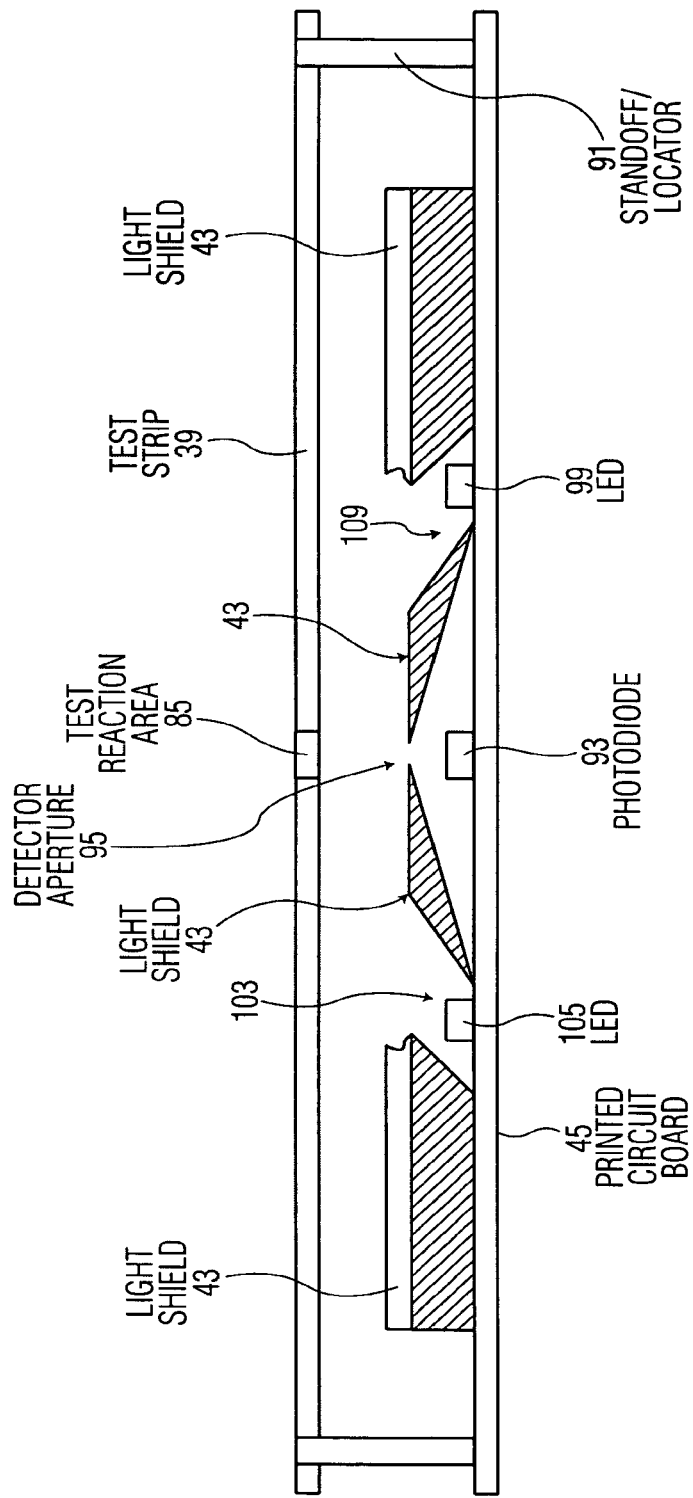
FIG. 14L is a simplified partial cross sectional view of the light shield taken along 14I-14I of FIG. 14F as mounted on a printed circuit board (PCB) in a simplified assembly.
Figure 14M:
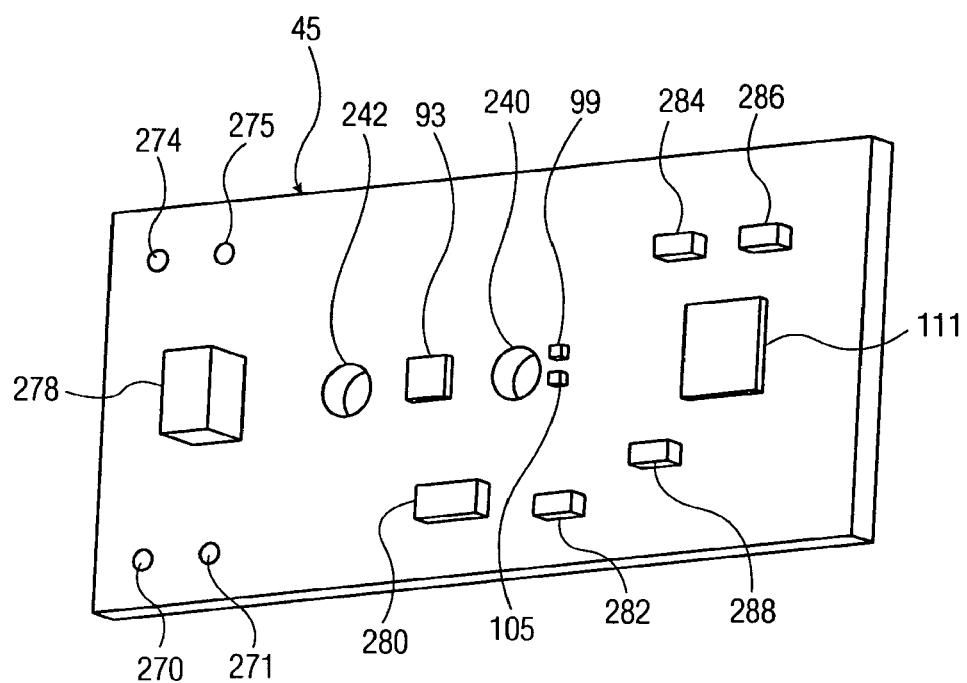
FIG. 14M is a top pictorial view looking toward the top of the printed circuit board (PCB) with components assembled thereon.

With further reference to FIG. 8, and to FIGS. 14A, 14B, and 14L, a subassembly of the fluidic and electronic portions of the device includes a sample wick 17 having an interior end securely mounted upon a portion of one end of a test strip 39, the other end of which has a portion secured to an interior end of an absorber strip 41. A portion of the test strip 39 is mounted on a light shield 43 proximate the absorber pad 41. The light shield 43 can be provided as a single molded plastic piece in this example, but as shown below is provided in two pieces for ease of manufacture and assembly. A printed circuit board (PCB) 45 has one portion mounted on the light shield 43. Note that FIG. 14M shows the arrangement of electrical/electronic components as mounted on the printed circuit board 45. Two batteries 47, 49, respectively, are mounted in a battery holder or compartment 66 at one end of light shield 43. As shown in FIGS. 8 and 14N, particularly, a pair of opposing apertures 68A and 68B in an interior wall of battery compartment 66 permit a pair of opposing battery contacts 70A and 70B, respectively, to be connected between the batteries 47 and 49, the printed circuit board 45. The liquid crystal display (LCD) 13 is secured via adhesive to a bottom face of a foam spacer 36, and the top face of spacer 36 is secured via adhesive on the bottom of PCB 45, in this example. With further reference to FIGS. 8, 14A and 14N, the test strip 39 is mounted on the bottom of light shield 43 as will described in greater detail below.

With further reference to FIGS. 8 through 11, the interior configuration 21 of the bottom half portion 18 of case 3 further includes a plurality of protruding rib portions 51, and a waffled or multiple cell region 53 configured along with the placement of the standoff sockets 23 to receive the bottom portion of the fluidic/electro-optical component assembly 40 in a secure manner. Similarly, the top half portion 10 of the casing 3 includes transverse wall separators 55, 56, 57, and 58 for snugly receiving therebetween the top portion of the fluidic/electro-optical component assembly 40. A waffled or multiple cell portion 59 is configured to provide a plurality of cells 61 therebetween, as shown. Note that the cells 61 in the top half portion 10, and cells 53 in the bottom half portion 18 of casing 3, respectively, provide a flood blocking area in the device for preventing excess urine flowing down the sample wick 17. Opposing triangularly shaped battery detents 63 and 64 are provided for providing clearance for batteries 47 and 49, respectively, for preventing movement and securing the latter in place.

Figure 11:
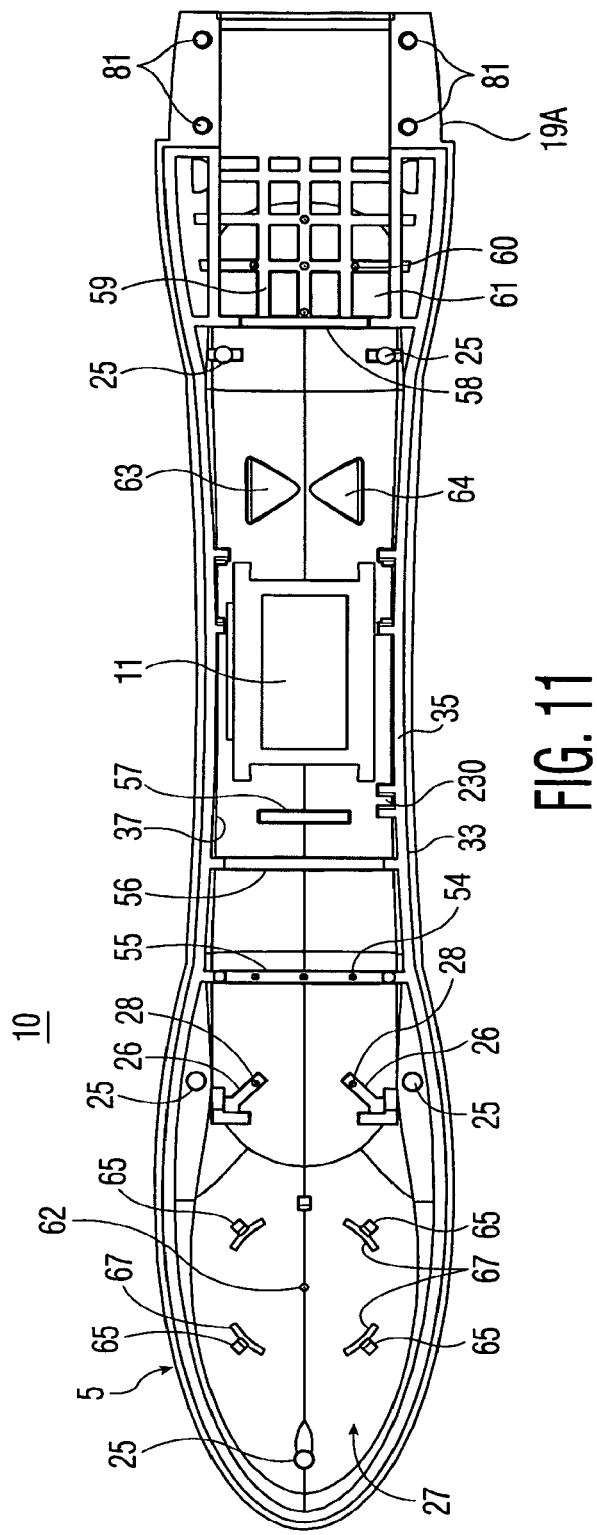
FIG. 11 is a plan view of the interior design of the top half portion of the casing for one embodiment of the invention.

With reference particularly to FIGS. 8, 9 and 11, the top half portion 10 of the casing 3 also includes in its interior cavity at the front end 5 a plurality of standoffs 65 each with an associated arc like or semicircular portion 67, and a standoff 69 arranged to snugly receive a desiccant pellet 71 (see FIG. 8). Also, the bottom half portion 18 of the casing 3 includes a reduced height rib portion 73 near the front end 3 for snugly receiving a portion of the desiccant 71. A barb 62 is centrally located between standoffs 65 for abutting against a central portion of desiccant pellet 71.

Figure 12:
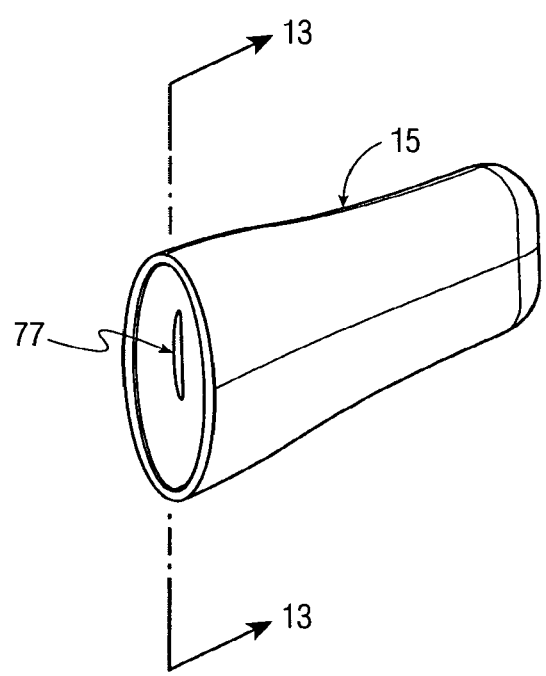
FIG. 12 is a perspective view of the cap for the casing of FIG. 1.
Figure 13:
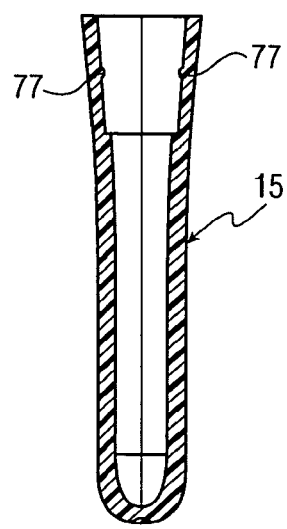
FIG. 13 is a cross sectional view of the cap taken along section line 13-13 of FIG. 12.

With reference to FIGS. 8, 12 and 13, the cap 15 is hollow, and includes on an opposing interior side wall portions relatively short ridge members 77. When the cap 15 is installed over the reduced end portions 19A, 19B of casing 3, the opposing ridges 77 snap into mating grooves 79 (see FIG. 8) located in opposing central portions of the reduced ends 19A and 19B of the top and bottom half sections 10, 18, respectively of casing 3. In this manner, the cap 15 is securely retained on the reduced end portion 19 of casing 3, yet can be easily removed for exposing the sample wick 17 for use of the device as previously described.

Figure 10:
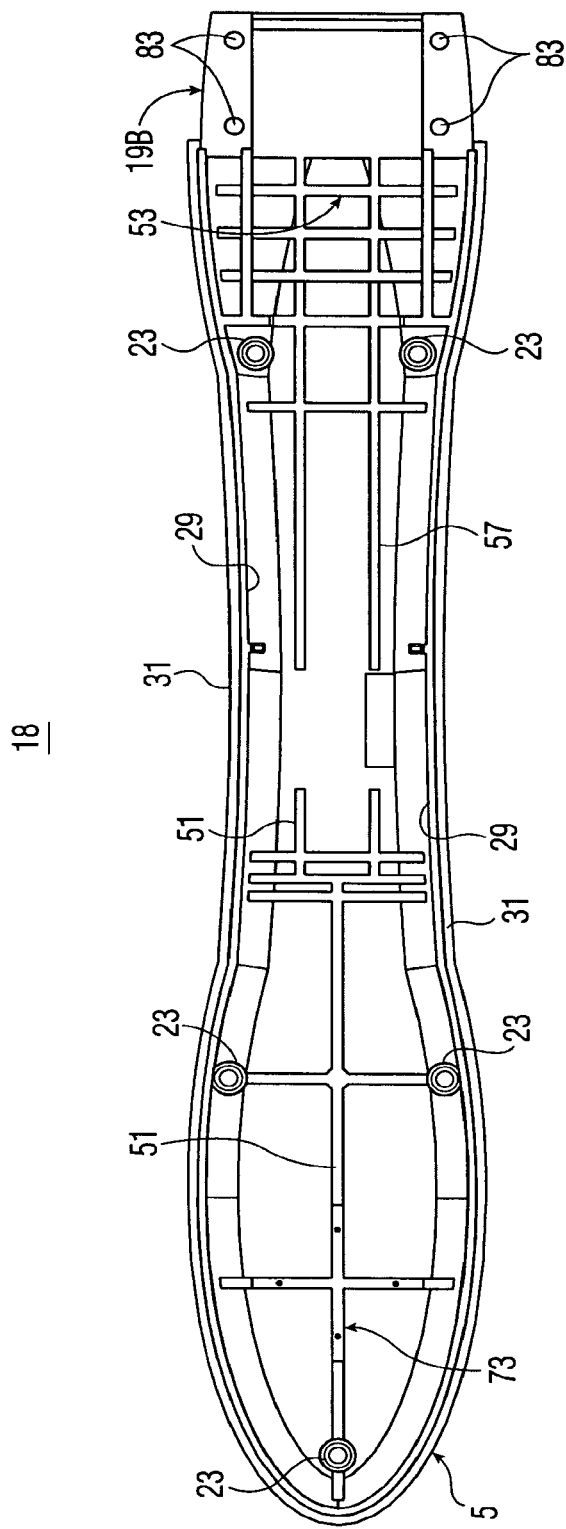
FIG. 10 is a top plan view of the interior design or configuration of the bottom half of the casing, a perspective view thereof being shown in FIG. 8, for an embodiment of the invention.

With reference to FIGS. 9, 10 and 11, the reduced portion 19B of the bottom half section 18 of casing 3 includes holes 83 for receiving pins 81 located on the reduced portion 19A of the top half section of casing 3. The opposing multi-contoured standoffs 26 located in the front interior portion 27 of the top half section of casing 3 are for snugly receiving extreme end portions of the absorber pad 41. The barbs 28 on standoffs 26, and barbs 54 on the top edge of wall separator 55 are for digging into absorber pad 41 to hold it in place. Similarly, the barbs 60 on the top edges of waffled portion 59 are for retaining the sample wick 17 in place.

With reference to FIGS. 14B, 14C, 14D, 14E, 14F, 14G, 14H, 14I, and 14M, in one embodiment of the invention, the light shield 43 is provided in one piece, and includes battery compartment 66 at one end as shown. Specifically, the light shield 43 includes as shown outer mounting rails 42R adjacent the right side, and 42L adjacent the left side, upon which the test strip 39 is mounted (also see FIG. 14D). The test strip 39 includes an alignment notch 200 (see FIG. 14N) for interacting with a registration tab 50 located on the right hand mounting rail 42R, as shown. By use of the alignment notch 200 and registration tab 50, the capture region 85 of the test strip 39 (see FIG. 17) is centered on a rectangular detector aperture 95 of the recessed bottom portion 44 of light shield 43. Strip guide walls 46 and 52 are provided at opposing portions of the right side. Other strip guide walls 48 and 202 are provided on an interior portion of the left side. Also, a standoff 76 is provided on the recessed bottom portion 44, for elevating the test strip 39 away from the recessed bottom portion 44 of light shield 43. The strip guide walls 202, 46, 48, and 52 retain and guide, via their interior portions, side edge portions of test strip 39. In one embodiment, rectangular apertures 103 and 109 are provided in the recessed bottom portion 44 for permitting light emitted from a red LED 99 and a green LED 105, respectively, to be directed onto the capture region 85 of the test strip 39. In an alternative embodiment, LEDs 99 and 105 can be located together in either one of apertures 103 and 109, or located separately in the apertures 103, 109. Accordingly, the alternative embodiment permits the elimination of one of the apertures 103, 109, whereby two apertures will remain either one of 103 and 109, and detector aperture 95. Note that the mounting rails 42R and 42L are extended above the recessed bottom portion 44 to provide sufficient space between the control region 85 of test strip 39 and apertures 103, and 109, and 95, to ensure that light from either aperture 103 or aperture 109 is readily directed onto the capture region 85, and reflected light therefrom is directed into detector aperture 95. The aforesaid gap between the control region 85 of test strip 39 and apertures 95, 103, and 109 is necessary for proper operation of the inventive device 1.

With further reference to FIGS. 14B through 14F, the light shield 43 further includes a retainer clip 204 having a living hinge 206, a locking finger 208, and a pair of retention fingers 210. Also, a roof member 212 is located on the opposing left side of the light shield 43 relative to retainer clip 204 on the right side thereof. During assembly of the present device, the test strip 39 of the fluidic assembly is positioned on the light shield 43 with the alignment notch 200 of the former positioned to receive the registration tab 50 of light shield 43. The test strip 39 is further positioned so that the roof member 212 captivates and overlays an edge portion of the former. After positioning the test strip 39 as indicated, the retainer clip 204 is moved upward for causing the retention figures 210 to overlay and retain an edge portion of test strip 39, with the locking finger 208 locked onto an edge portion 214 of the outer wall on the right hand side of the light shield 43, as shown. Note further that an index tab 216 on test strip 39 (see FIG. 14N) is further included for being received in a locating slot or channel 218 provided on the left side of light shield 43, as shown, for further aid in proper aligning test strip 39 onto light shield 43. A raised hat or c-shaped platform member 220 is provided for ensuring in the assembled device a positive mechanical support for test strip 39 to maximize the transfer of urine therebetween. Standoffs 222 and 224 are provided on opposing sides of the battery compartment 66 portion of the light shield 43 to assist in assembling the test strip 39 and associated fluidic assembly onto the light shield 43. An opening 226 is provided through the portion of the battery compartment 66 for permitting the pointed free end portions of electrical contacts 72 and 74 of the fluidic switch to protrude out of the opening 226, for penetrating into a portion of the test strip 39, for sensing the presence of urine as will be described in detail below. Note that the electrical contacts 72 and 74 are assembled onto the printed circuit board 45, as explained below. Also note that a locating stud 228 is provided on the right side of light shield 43 for mating with a locating keyway 230 (see FIGS. 9 and 11) in the top half portion 10 of casing 3, for accurately locating the light shield assembly in the case 3. In addition, as partially shown in FIG. 14C, a heat seal connector 207 provides electrical connections between LCD display 13 and printed circuit board 45.

In the embodiment of the invention where the light shield 43 is provided in two pieces, an inner light shield 43A, and an outer light shield 43B, which are mated together as shown in FIG. 14N, include a locating groove 232 (see FIG. 14C) in an interior wall portion of the right side of outer light shield portion 43B, for receiving a portion of the registration tab 50 for proper positioning of the inner light shield 43A into the outer light shield 43B. Otherwise, as previously indicated, the light shield 43 can be provided in one piece. In addition, clearance holes 234 and 236 are provided in an extended portion of the battery compartment 66, for providing clearance holes for battery contacts 70A and 70B, respectively (see FIGS. 14C and 14N). Note that in the light shield 43 a hole 238 is shown, which is merely a mold feature, and as such is nonfunctional.

FIG. 14E shows a pictorial view of the light shield 43 looking toward the top and right side surfaces, and a portion of the front side thereof. As shown, the detector aperture 95, in this example has a relatively large opening on the top surface as compared to the size of the rectangular opening on the bottom surface (see FIG. 14D), with the walls 94 of the aperture 95 forming a hollow pyramid shape from the top, as shown in FIGS. 14E, 14F, and 14I. The detector aperture 95 collects light reflected from the capture region 85 of test strip 39 resulting from energization of either one of LEDs 99 or 105 (see FIG. 14M). The aperture 95 portion on the recessed bottom surface 44 (see FIG. 14C) is purposely configured for blocking extraneous light waves from entering the photodetector at 93 (see FIG. 17). A pair of opposing alignment pins 54 and 56 (see FIGS. 14E through 14F and 14N) are provided on opposite sides of the photodetector aperture 95 on the top surface as shown. The alignment pins 54 and 56 are received by alignment holes 240 and 242 on PCB 45, respectively, for ensuring proper alignment thereof when it is mounted upon the top surface of light shield 43. The PCB 45 can be rigidly secured via its top surface to the top surface of light shield 43. With reference FIG. 14M, showing a top plan view of PCB 45, note the positioning of red LED 99, photodetector 93, and green LED 105, on the top surface of PCB 45, in this example. Note also the positioning of the alignment holes 240 and 242 through PCB 45. When the top surface of PCB 45 is aligned as previously described, and mounted on the top surface of light shield 43, the photodetector 93 will be centered within aperture 95, red LED 99 centered in aperture 109, and the green LED 105 centered in aperture 103 on the top surface of light shield 43, in one embodiment. In another embodiment LED 99 and LED 105 may be located together in one of apertures 103 and 109. Note that the recessed areas 244 and 246 in the top surface of light shield 43 reduce the amount of material required for the light shield 43 in order to provide clearance for components placed on the surface of PCB 45. This recessed region 244 and 246 can be more clearly observed in FIGS. 14E and 14F of light shield 43. Note that in the preferred embodiment, the PCB 45 and light shield 43 are configured for snapping together. Also, retention fingers 254 and 256 are provided for retaining distal edge portions of PCB 45.

With further reference to FIGS. 14E and 14F, a retention finger 248 is provided for retaining batteries 47 and 49 in battery compartment 66. Also, battery contact stops 250 and 252 are provided within battery compartment 66 for preventing rotational movement of battery contacts 70A and 70B, respectively.

FIGS. 14G and 14H show right and left side elevational views of light shield 43, respectively. Also, FIGS. 14J and 14K show front and back elevational views of light shield 43.

With reference to FIG. 14I, a longitudinal cross sectional view taken along 14I-14I of FIG. 14F is shown. Particularly note that apertures 103 and 109 are configured along their interior surfaces for receiving LEDs 105 and 99, respectively, in a manner for directing light therefrom to the bottom surface of light shield 43 for maximizing to the greatest extent possible the intensity of light therefrom onto the capture region 85 of test strip 39, for one embodiment. Note the simplified partial cross sectional diagram of FIG. 14L, generally showing the physical configuration between the LEDs 99, 105 and apertures 109, 103, respectively, and capture region or test reaction region 85, for one embodiment of the invention. Also shown is the configuration between photodetector aperture 95, photodiode 93, and capture region 85.

Figure 22:
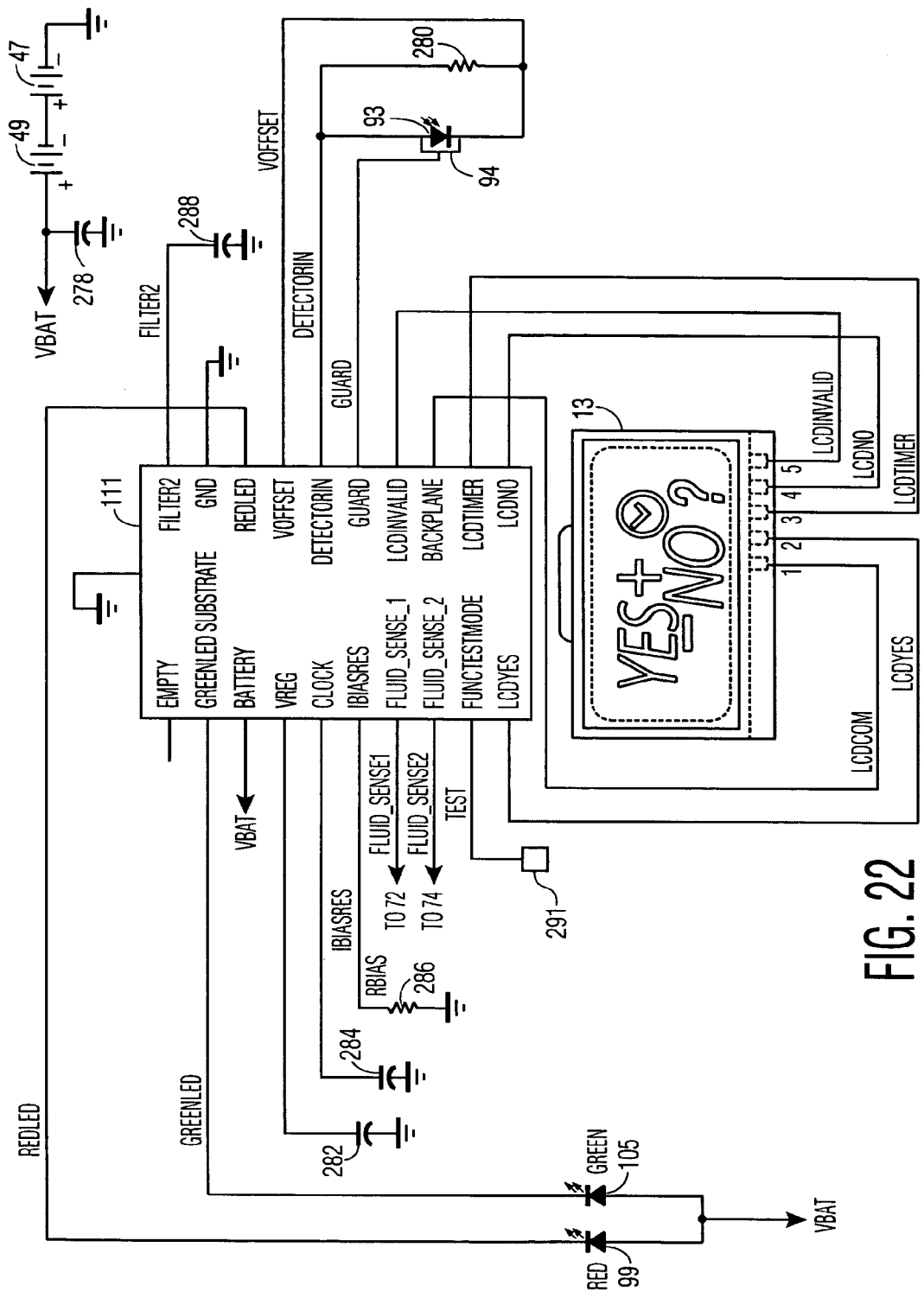
FIG. 22 shows a circuit schematic diagram of the electronic system for an embodiment of the invention.

The layout of components on the PCB 45 will now be described with reference to FIG. 14M. FIG. 14M is a pictorial view looking toward the top showing the printed circuit board 45 with components mounted thereon. The components shown include capacitors 278, 282, 284, and 288, respectively; resistors 280 and 286, respectively; photodetector 93; and light emitting diodes 99 and 105, respectively. Note that a circuit schematic diagram showing interconnection of these components on the printed circuit board 45 is shown in FIG. 22, as described in greater detail below. Also, vias or conductively coated holes 270 and 271 are provided through the PCB 45 for receiving tabs 272 and 273, respectively of electrical contact 70A. Similarly, vias or holes 274 and 275 are located in PCB 45 for receiving tabs 276 and 277, respectively of electrical contact 70B.

An exploded assembly view of the electromechanical portions of the device 1 is shown in FIG. 14N. More particularly, FIG. 14N shows an exploded assembly view of the fluidic/electro-optical component assembly 40 of FIG. 14A. In this example, an embodiment is shown for providing light shield 43 from two molded plastic pieces including an inner light shield 43A configured to fit into and securely mate with an outer light shield 43B. This provides more economic manufacturing, although a single piece light shield 43 is preferred. Note that for purposes of simplification, not all of the components, such as LEDs 99 and 105, are shown.

Figure 15:
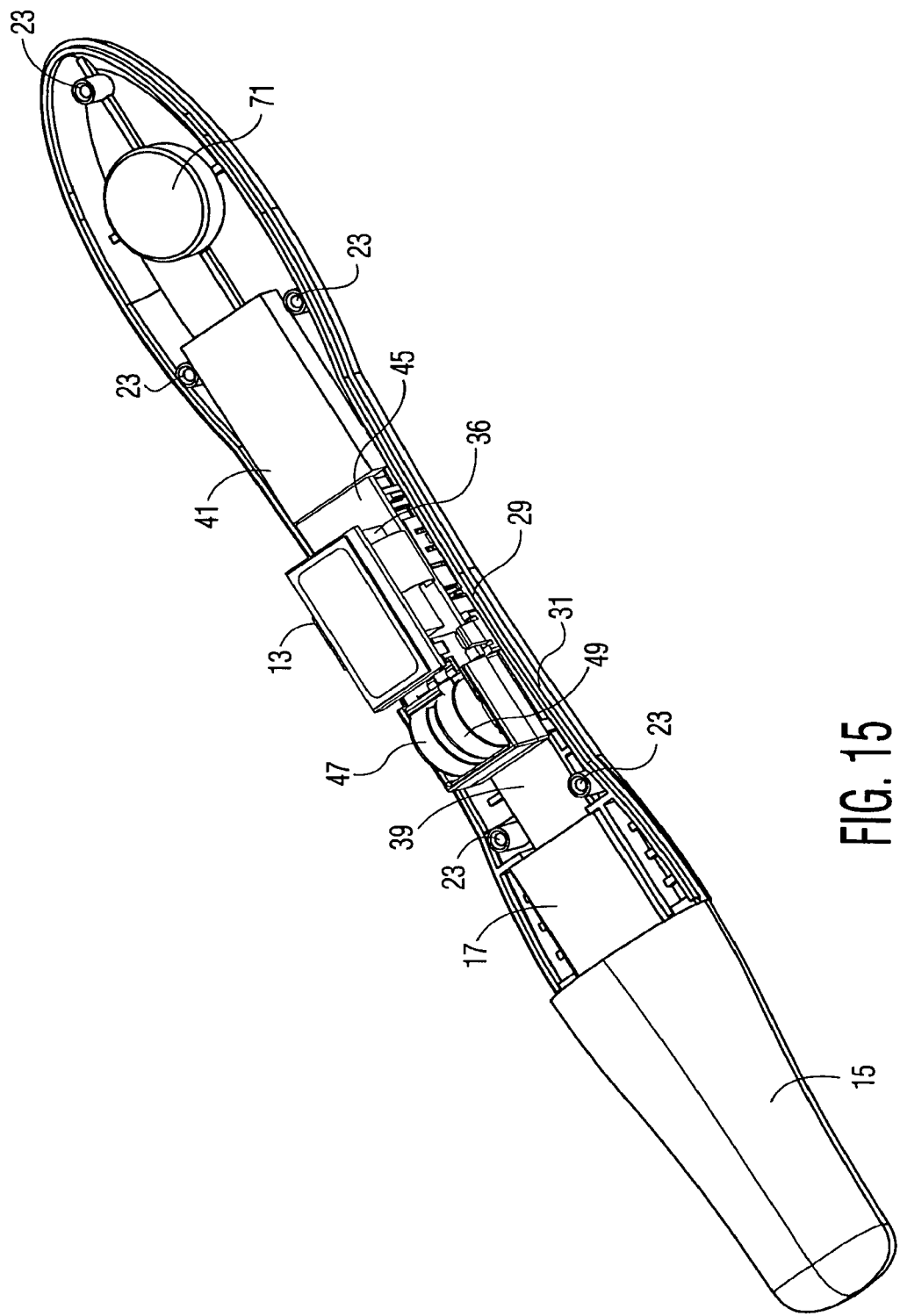
FIG. 15 is a perspective view looking toward the top and left-hand side of the device with the top half of the casing removed.
Figure 16:
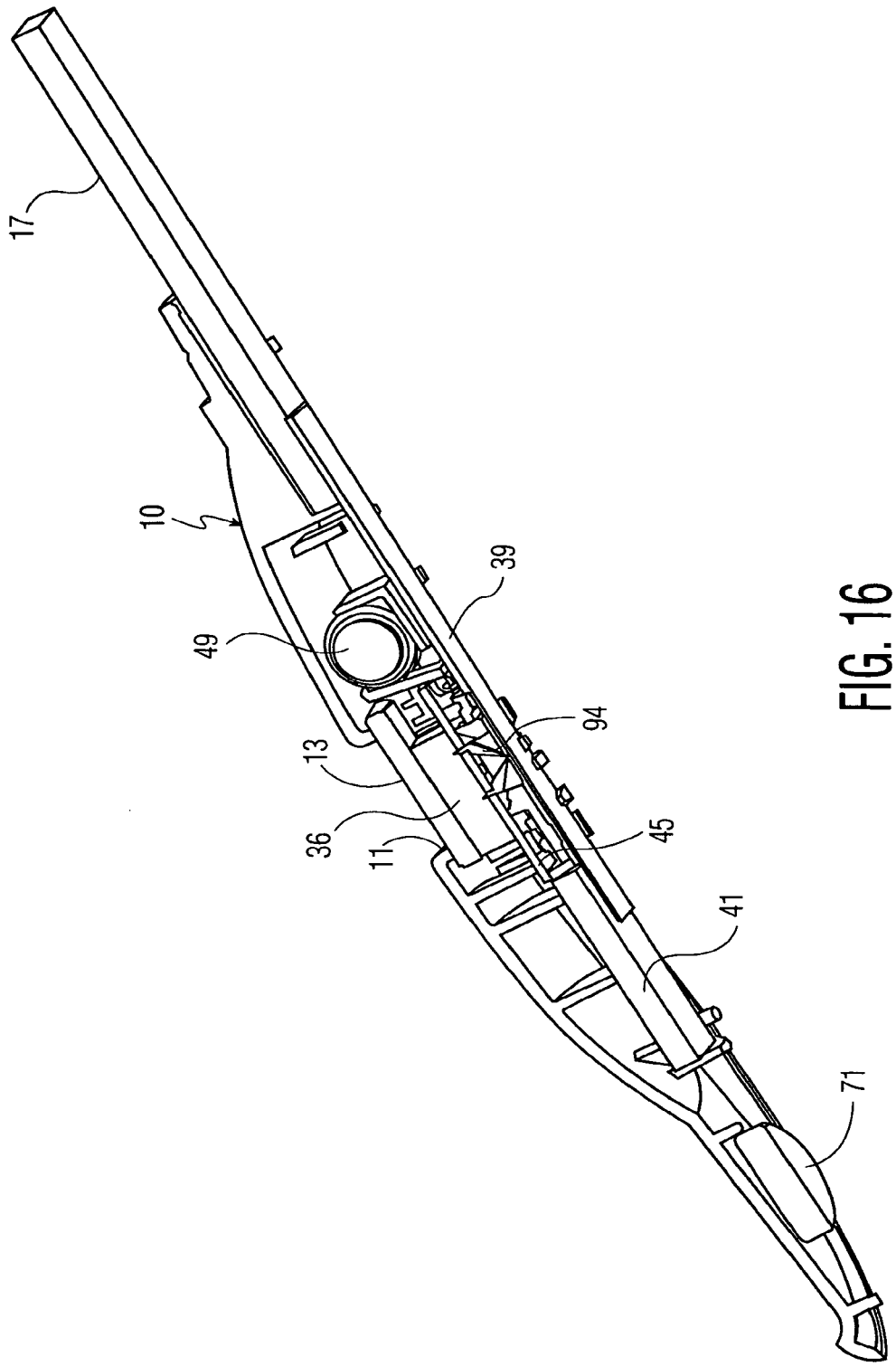
FIG. 16 is a partial cutaway cross sectional perspective view taken along 16-16 of FIG. 2 of the present device looking toward the bottom right side of the present device.

FIG. 15 shows a pictorial view of the assembled device 1 with the top half section 10 of the casing 3 partially removed. In other words, FIG. 15 is a partial transparency view looking through the top half section of the casing 3 of the assembled device 1. FIG. 16 shows a partial cutaway cross sectional view taken along line 16-16 of FIG. 2, with the bottom half section 18 of the case 3 and the cap 15 removed.

The present inventive device 1 provides an easily readable display in words, in the examples given, for indicating the presence or absence of an analyte, such as human chorionic gonadotrophin (hCG) or luteinizing hormone (LH), in a urine stream. With reference to the above-given description, the present device 1 comprises an outer casing 3 enclosing amongst other components assay material carried on a test strip 39. With reference to FIG. 14A, assay material in the test strip 39 defines a capture region located beneath the light shield 43 for binding an analyte of interest, i.e., hCG or LH. In one embodiment of the invention, as shown in FIGS. 8 through 11, reduced portions 19A and 19B of the top and bottom half sections 10, 18, respectively, of the casing 3 include a honeycomb configuration or cells 59, 53, respectively, that serve to collect excess urine for preventing flooding of the device by an excess of urine being applied to the sample wick 17. In this manner, flood blocking is provided in the device 1. The cells 53 and 59 collect the excess urine.

From the foregoing, preferred embodiments of the invention device 1 have been shown and illustrated. However, the outer casing 3 of the device and light shield 43 may take various forms. Typically, the case 3 will comprise an elongated casing having interfitting parts made of moisture impervious solid materials, for example, a plastic material. It is contemplated that a variety of commercially available plastics, including, but not limited to, polyvinyl chloride, polypropylene, polystyrene, polyethylene, polycarbonates, polysulfanes, polyesters, urethanes, and epoxies can be used to produce casing 3 and the light shield 43 useful in the practice of the instant invention. Note that ABS is the preferred plastic material for the light shield 43. The device casing 3 and light shield 43 can be prepared by conventional methodologies, for example, standard molding technologies well known in the art. Such molding technologies can include, but are not limited to, injection molding, compression molding, transfer molding, blow molding, extrusion molding, foam molding, and thermoform molding. The aforementioned molding technologies are well known in the art, and as such are not discussed in detail herein. See for example, *Processes And Materials Of Manufacture*, Third Edition, R. A. Lindsberg (1983) Allyn and Baron pp. 393-431.

Figure 17:
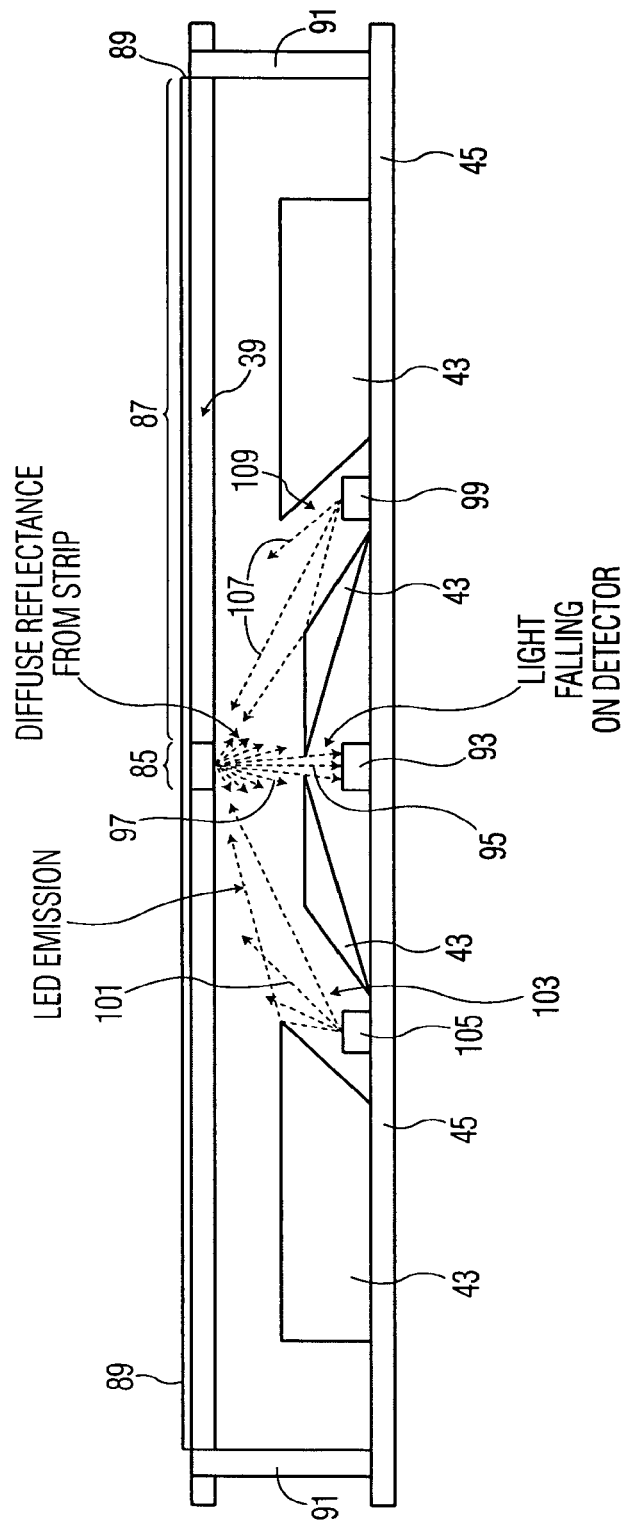
FIG. 17 is a simplified diagram showing the basic operating principles of the present device.

With reference to FIG. 17 showing a simplified diagram of certain operating principles of the present device 1, the test strip 39 is shown to include a capture region 85 centrally located under the light shield 43 (also see FIG. 14A). Accordingly, the capture region 85 is disposed upon assay material in the test strip 3 downstream of the analyte capture region represented by sample wick 17. Preferred reagents for use in the test strip 39 are described in U.S. patent application Ser. No. 08/432,894 filed on May 2, 1995, the disclosure of which is incorporated herein by reference to the extent that it does not conflict herewith. Note that as used herein, the term "assay material" means any material, preferably absorptive material, that can be used to detect a presence of a preselected analyte in a urine sample. Also, as used herein the term "capture region," such as region 85, means a region of the assay material capable of binding, either directly or indirectly, the preselected analyte. During direct binding, the preselected analyte binds to an immobilize binding partner, for example, an anti-analyte antibody immobilized within the capture region 85 of the assay material or test strip 39. During indirect binding, the preselected analyte binds to a binding partner, for example, an anti-analyte antibody biotin conjugate, and the binding partner binds to a capture component, for example, streptavidin, immobilized within the capture region 85 of the test strip 39. As previously mentioned, by means of sorptive transport, urine applied to the sample wick 17 via a urine stream is transported from the sample wick to the test strip 39, and flows through the test strip 39 and capture region 85 to the absorber pad 41 for collecting the urine from the test strip 39. In the preferred embodiment of the present invention, the assay material comprises three elements, the sample wick 17, test strip 39, and absorber 41, but this particular design configuration is not meant to be limiting. Alternatively, a single element of wicking or sorptive material can be used, through appropriate alterations in other aspects of the design of the present device 1. In the preferred embodiment illustrated, the sample wick 17 is provided by a urine sample absorbent material, as appropriate. Test strip 39 is provided through use of a biphasic chromatographic substrate. A reservoir absorbent material is provided for absorber pad or strip 41. The material requirements for the sample wick 17, test strip 39, and absorber strip 41, are known in the art and described in U.S. Pat. No. 6,319,676, previously mentioned above.

In the preferred embodiment, the sample wick 17 consists of bibulous hydrophilic material to facilitate absorption and transport of a urine sample to the biphasic chromatographic medium. Such materials may include cellulose acetate, hydrophilic polyester, or other materials having similar properties. A combination of absorbent materials also may be used. Preferred materials include bonded cellulose acetate, bonded polyolefin or hydrophilic polyester, such as those materials commercially available from American Filtrona Company (Richmond, Va.). Other preferred materials include absorbent papers such as Ahlstrom 939 or Ahlstrom 1281. The sample wick 17 preferably is coated with a buffered solution containing bovine serum albumin (BSA) and a non-ionic surfactant, such as Triton X-100®. The presence of BSA and a surfactant minimize non-specific absorption of the analyte. A concentration of about 3% BSA and about 0.1% surfactant are effective for this purpose.

Also, the preferred embodiment of the invention includes a biphasic chromatographic substrate with a test strip 39. For ease of illustration, reference is made to FIG. 17. The substrate includes a release regent media 87 adjacent the capture regent media 85. As taught in U.S. Pat. No. 6,277,650, a release regent media 87 preferably comprises absorbent paper, and the capture medium or region media 85 preferably comprises a nitrocellulose membrane. Although not specifically shown herein, as taught in the aforesaid patent, the release region media 87 and capture region media 85 preferably are both laminated onto an opaque plastic film or sheet 89. Disposed upon the release region media 87 is a first binding member comprising a first monoclonal antibody reactive with a first epitope on the analyte, and labeled with a visually detectable marker, such as, colloidal gold particles, and a capturable component comprising a biotinylated monoclonal antibody disposed downstream of the labeled antibody. In this example, the color of the marker is purple. The biotinylated antibody is reactive with a second epitope on the analyte and is capable of forming a complex with the labeled antibody and the analyte. Also disposed upon the test strip 39 is a capture region site 85 for capturing and immobilizing the complex, as previously mentioned. The capture region 85 immobilizes thereon a capture component, preferably streptavidin, which has a high affinity for the biotin portion of the complex.

A method for manufacturing the preferred biphasic chromatographic medium is described in the above-cited U.S. Pat. No. 5,846,835, the disclosure of which is incorporated herein by reference as previously mentioned. Briefly, the release region media 87 and the capture region media 85 are positioned such that they overlap slightly, and an adhesive is disposed on the back of each (the back being the side opposite that which will receive reagents). The adhesive may be any pressure sensitive or hot melt adhesive which does not fill the pores of the release or capture region, thereby permitting unimpeded flow of the solvent front through the medium. Adhesives useful in the present invention are commercially available for example, from Adhesives Research Corporation. In a currently preferred embodiment, the adhesive is disposed on a opaque polymer backing. The overlapping release and capture regions media 87, 89, respectively, then are packed through laminating rollers of a laminating machine together with the backed adhesive, forming a laminate of the capture and release media, the adhesive and the polymer backing. The resulting laminated biphasic substrate forming test strip 39 then is ready to receive the reagents, which are disposed as "stripes" onto the top of the substrate. Once the reagents have been deposited and dried, if necessary, the substrate is cut into desired size.

The diffusive and non-diffusive reagents can be applied to the release and capture reagents by any well known technique. In a currently preferred embodiment, the diffusable antibody reagents are applied to the release region 87 by direct application onto the surface of the medium and dried to form a narrow band. The non-diffusable reagents are applied to the capture region 85 by passive adsorption.

The preferred embodiment further comprises, an absorber 41 consisting of absorbent material disposed distal to, or downstream of, the biphasic chromatographic substrate or test strip 39 and in fluid communication therewith. The absorber 41 provides a reservoir of absorbent material disposed beyond the test strip 39, for absorbing and drawing a relatively large volume of the urine and any analyte it contains through the test strip 39 to aid sensitivity. The reservoir absorbent material preferably comprises a hydrophilic material which may be the same as the urine sample application region absorbent. The purpose of the absorber 41 is to facilitate capillary action along the chromatographic substrate of test strip 39, and to absorb excess urine contained with the casing 3. The reservoir absorbent material preferably comprises absorbent paper made from cotton long linter fibers, such as identified by product codes S&S 300, S&S 470, and S&S 900 (available from Schleicher & Schuell, Inc.) or cellulosic materials, such as Whatman 3MM (available from Whatman).

During operation of the preferred embodiment, the cap 15 is removed, and urine typically from a urine stream is deposited onto the exposed sample wick 17. The urine then passes by sorptive transport, for example, capillary action, wicking, or simple wetting, from the sample wick 17 to the biphasic chromatographic material of test strip 39, and finally to the reservoir material of absorber 41. During transportation through the test strip 39, the urine initially contacts the first monoclonal antibody located on the release region 87 (see FIG. 17). Upon contact with the urine, the first monoclonal antibody becomes reconstituted in the urine and then reacts with a first epitope on the preselected analyte, provided that the analyte is present within the urine sample. The first monoclonal antibody is labeled with a visually detectable marker such as colloidal gold. The urine while moving towards the capture region 85 contacts the second monoclonal antibody also located in the release region 87. Upon contact with the urine, the second monoclonal antibody also becomes reconstituted in the urine, and then reacts with the second epitope on the preselected analyte. The second monoclonal antibody is labeled with a capturable component such as biotin. The analyte, first monoclonal antibody, and the second monoclonal antibody, therefore, react to form a complex which subsequently can be captured when the complex reaches the capture region 85 and contacts the streptavidin immobilized within the capture region 85.

Broadly, the device and method of the invention may be used to detect any analyte which has heretofore been assayed using known immunoassay procedures, or is detectable by such procedure, using polyclonal antibodies or fragments thereof, monoclonal antibodies or fragments thereof, biosynthetic antibody binding sites or other proteins. Various specific assay protocols and reagents are known per se, see for example, U.S. Pat. No. 4,313,734, and U.S. Pat. No. 4,366, 241.

It is, therefore, contemplated that chemical aspects of the invention are not limited by the precise nature of the binding members. For example, polyclonal antibodies and fragments thereof or biosynthetic antibody sites, such as those disclosed in U.S. Pat. Nos. 5,091,513, and 5,132,405, and 5,258,498 may be substituted for the monoclonal antibodies disclosed herein. Accordingly polyclonal antibodies, monoclonal antibodies or biosynthetic antibody binding sites having specific binding properties and high affinity for virtually any antigenic substances which are useful in the present invention as binding and capture materials are publicly known and available. Alternatively, preferred monoclonal antibodies, polyclonal antibodies, or biosynthetic antibody binding sites may be prepared using techniques well known and thoroughly disclosed in the art. The literature is replete with protocols for producing and immobilizing antibodies. For example, the preparation of polyclonal and monoclonal antibodies is disclosed in *Antibodies, A Laboratory Manual* (1988) Harlow and Lane, Cold Spring Harbor Press. The preparation of biosynthetic antibody binding sites is described in U.S. Pat. Nos. 5,091,513, and 5,132,405, and 5,258,498. Methods for immobilizing proteins are described in *Laboratory Techniques In Biochemistry And Molecular Biology*, Tijssen, Vol. 15, Practice And Theory Of Enzyme immunoassay, Chapter 13, Immobilization of Immunoreactants on Solid Phases, pp. 297 through 328 and all the references cited therein.

The electro-optical embodiments of the invention will now be discussed in greater detail with further reference to the simplified diagram shown in FIG. 17. The single piece light shield 43 is mounted on the printed circuit board 45, as shown. Two pairs of standoffs 91 are used for securing the test strip 39 to the printed circuit board 45, with the test strip 39 being positioned a predetermined distance or spacing from the light shield 43, as shown. A photodiode 93 is mounted on the printed circuit board 45 at a position that is below a detector aperture 95 of light shield 43 for receiving light rays 97 reflected from the capture region 85 and directed through the aperture 95. A red LED 99 (light emitting diode having a wavelength in the red color region, [typically 660 nm (nanometers), in a range of 640 nm to 680 nm] is mounted on printed circuit board 45 in a position for permitting light waves 107 emitted therefrom to be directed through a guide path 109 provided by light shield 43 onto capture region 85. Also, a green LED 105 is mounted on printed circuit board 45 at a position for emitting light waves 101 having a wavelength in the green color region (typically 565 nm, in a range of 560 nm to 570 nm) to be guided through a guide path 103 of light shield 43 for directing green light onto the capture region 85. Accordingly, the light shield 43 is designed to provide multiple functions, including guiding red light waves emitted by LED 45 to the capture region 85 serving as a test target area, to guide green light emitted by LED 105 to the capture region 85, to provide an aperture 95 for both permitting reflected light rays from the capture region 85 to be directed onto the photodetector 93 while simultaneously rejecting background reflections, and to provide a means for facilitating the location of the optical components in test strip 39 an appropriate three dimensional relationship with one another. Note that the invention is not meant to be limited to a red LED 99 and a green LED 105, but the LEDs must have easily detectable different respective wavelengths. A green LED is used for LED 105 rather than a blue LED to obtain a lower cost for device 1, although it has been found that a blue LED in the range of 505 nm to 540 nm can provide increased sensitivity.

Figure 18:
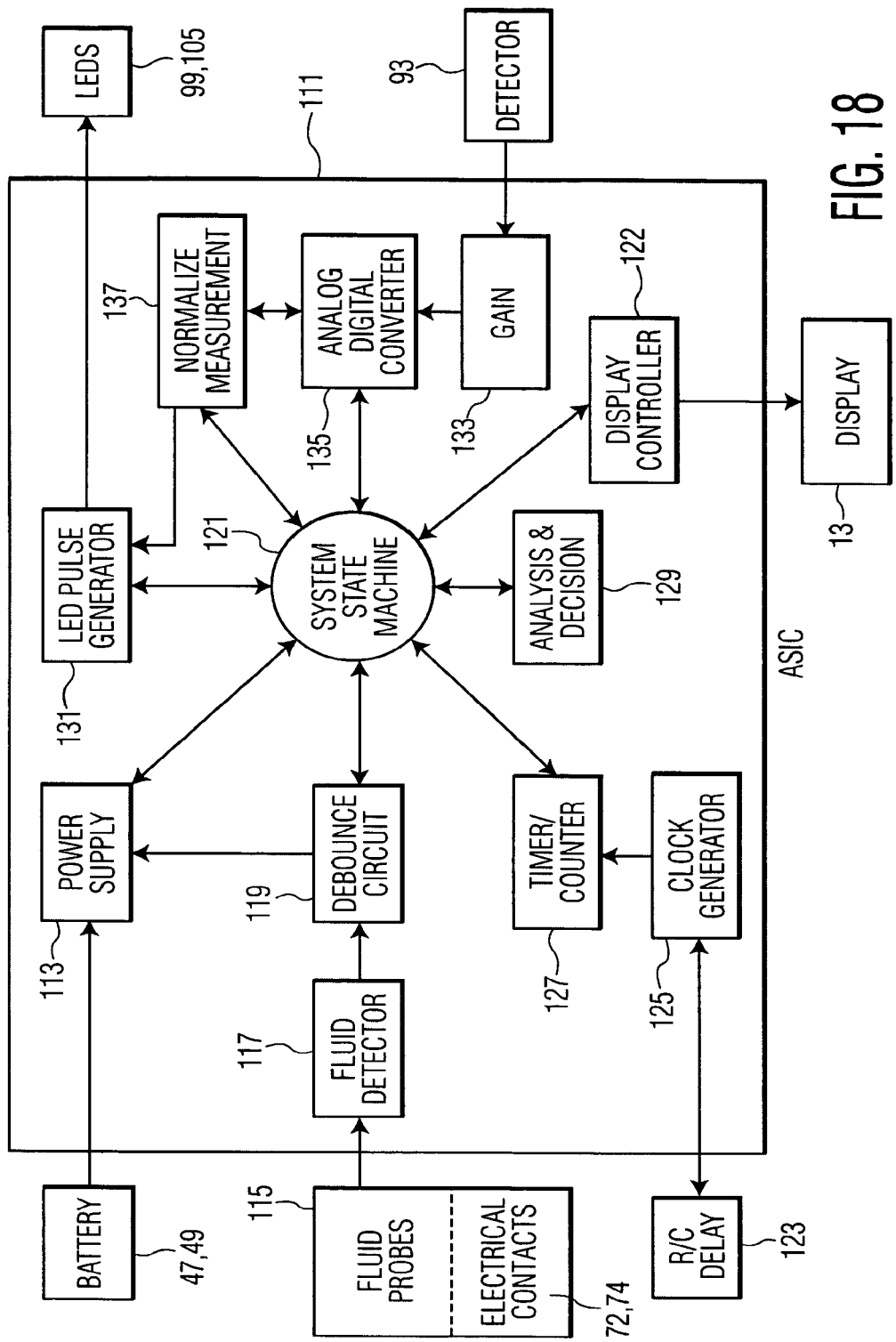
FIG. 18 is a block schematic diagram for the present device including an Application Specific Integrated Circuit (ASIC) for one embodiment of the invention.

The block schematic diagram of device 1 for showing the interconnection between various components and functional aspects of the electronic portion thereof is shown in simplified form in FIG. 18. An Application Specific Integrated Circuit (ASIC) 111 is included on the PCB 45 for providing electronic circuitry and digital networks necessary for operating device 1. Components that interact with the ASIC 111 include a battery represented by a pair of batteries 47, 49, that are alkaline button cells as normally used in watches, and hearing aids. For example, batteries 47 and 49 can be provided by LR41H button cells manufactured by Golden Power Industries Ltd. The batteries 47, 49 provide DC power to the internal power supply 113 of ASIC 111. The fluid switch or Fluid Probes 115 are provided by a pair of spaced apart electrical contacts 72 and 74 secured to the printed circuit board 45 at a position for contacting the surface of test strip 39 proximate sample wick 17, as previously described. The Fluid Probes 115 are connected to a Fluid Detector 117 of ASIC 111. Fluid Detector 117 detects the flow of electrical current caused by a drop in the electrical resistance between contacts 72, 74 due to the presence of urine in the test strip 39. When such current flow is detected, the Fluid Detector 117 provides an output signal to the Debounce Circuit 119 which responds to the output signal from the Fluid Detector 117 by turning on power to the ASIC 111. A time delay circuit 123 provided by a capacitor 284 to the "clock" pin on the ASIC 111, and the other end to a source of reference potential, ground in this example. The R/C Delay circuit 123 functions to provide a time constant for the clock generator 125 of ASIC 111, which operates to provide a clock or timing signal to a Timer/Counter digital network 127, the latter being connected to the System State Machine 121. The Analysis & Decision Network 129 operates via an algorithm to analyze signals provided from the System State Machine 121, and to provide results of this analysis in the form of decision signals back to System State Machine 121. Based upon this result, System State Machine 121 drives the display controller 122 to output the appropriate result to operate display 13. During operation of the device 1, when fluid is detected, that is when urine is detected on the test strip 39 via the Fluid Probes 115, Fluid Detector 117 driving Debounce Circuit 119, connected to the System State Machine 121 responds in a manner described in greater detail below.

In general or broad terms, the System State Machine 121 operates a LED Pulse Generator 131 to selectively provide an energizing or drive pulse of predetermined duration to the red LED 99, or to the green LED 105, at appropriate times, as will be further described. The Detector 93 is a photodiode, as previously described, for detecting reflected light from capture region 85 of test strip 39. The signal from the Detector 93 is an analog signal that is inputted to the Gain Circuit 133 of ASIC 111. As will be described in greater detail, the Gain Circuit 133 operates to both amplify the red reflected signals and green reflected signals over a given test time. The output of the Gain Circuit 133 is provided to an Analog-to-Digital Convertor network 135 which converts the signal to a digital signal. The digitized signal is provided to both the System State Machine 121, and to a Normalize Measurement Circuit 137 which normalizes the digitized signal, and provides the same to the System State Machine 121.

Figure 20:
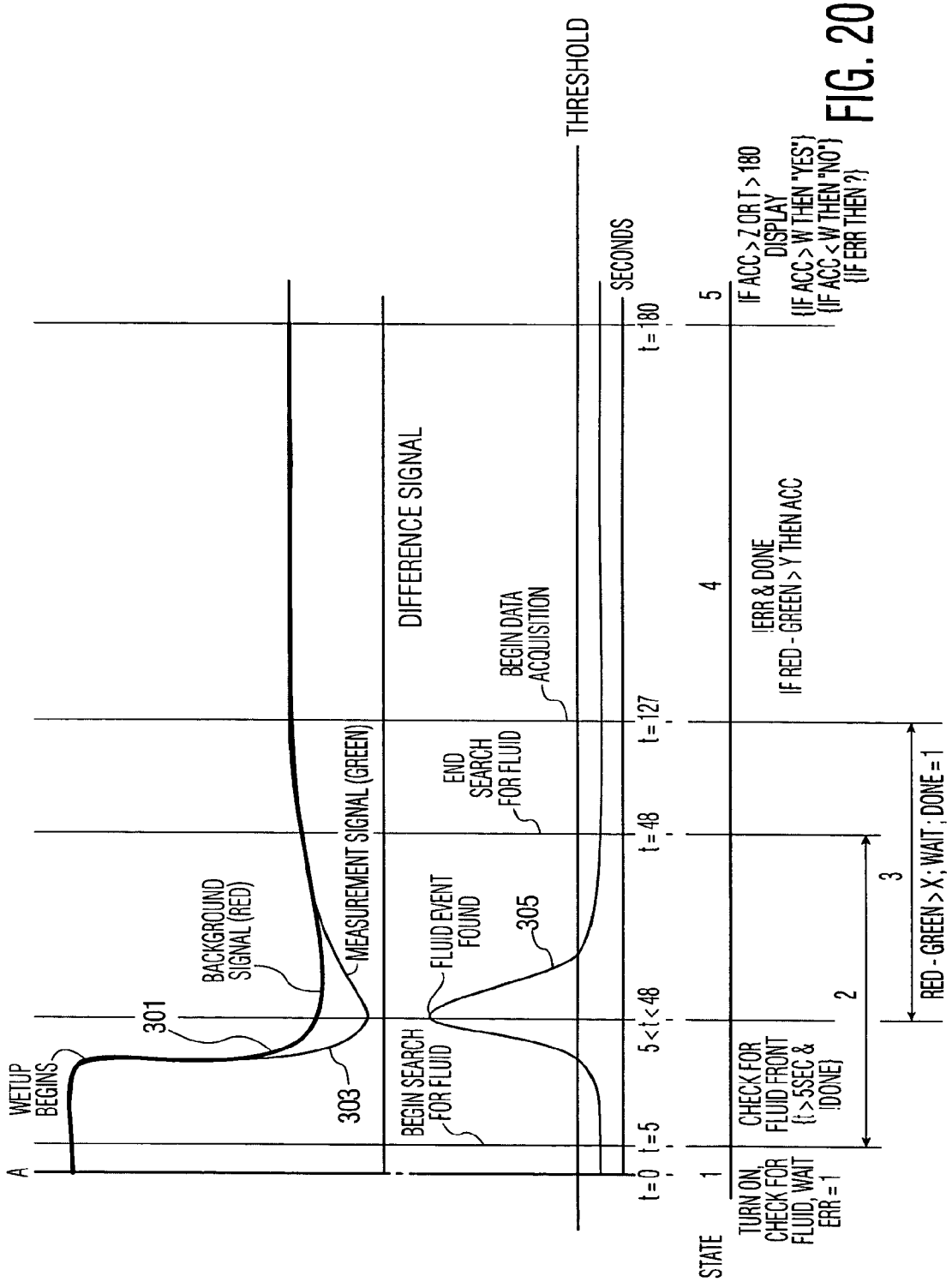
FIG. 20 shows interrelated curves for a "Negative Response Waveform," the resultant "Difference Signal" curve, and the association "State" diagram relative to different periods of time in conducting a test with the present device for one embodiment of the invention.
Figure 21:
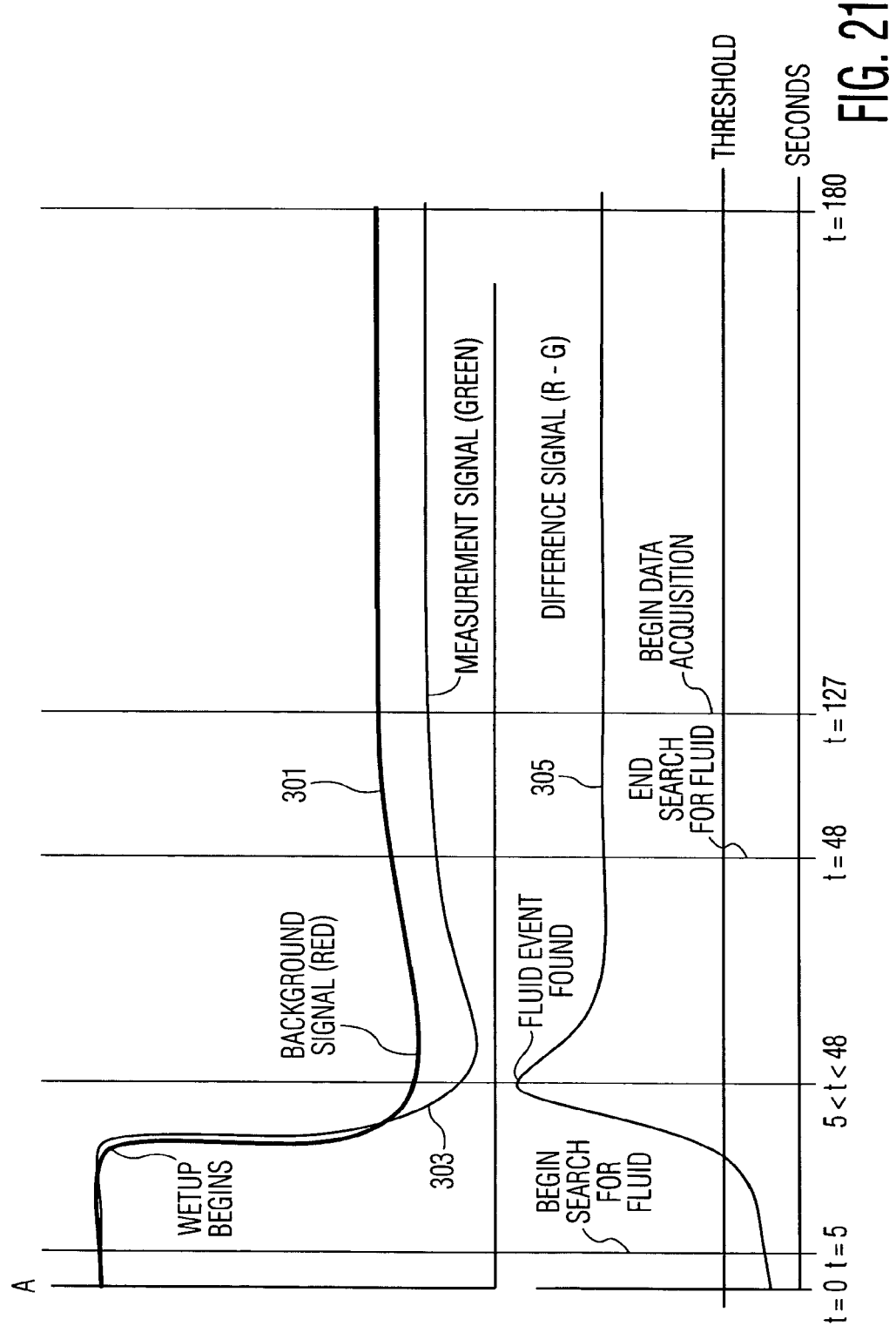
FIG. 21 shows a "Positive Response Waveform," the resultant "Difference Signal" and associated waveforms obtained from an illustrative device test run.

FIGS. 20 and 21 will now be described in greater detail. FIG. 20 shows an example of the waveforms associated with detecting the absence of a preselected analyte in a urine stream, in this example. The waveforms of FIG. 21 are related to an example of a test routine that detects the presence of a preselected analyte in a urine stream. More specifically, the pulsing of the red LED 99 causes the waveform 301 to be produced, and the pulsing of the green LED 105 causes the waveform 303 to be produced, as previously described. If the preselected analyte is not present in the urine stream, difference signal 305 shown in FIG. 20 is produced, whereas if the analyte is present, the difference signal 305 shown in FIG. 21 is produced.

Figure 19:
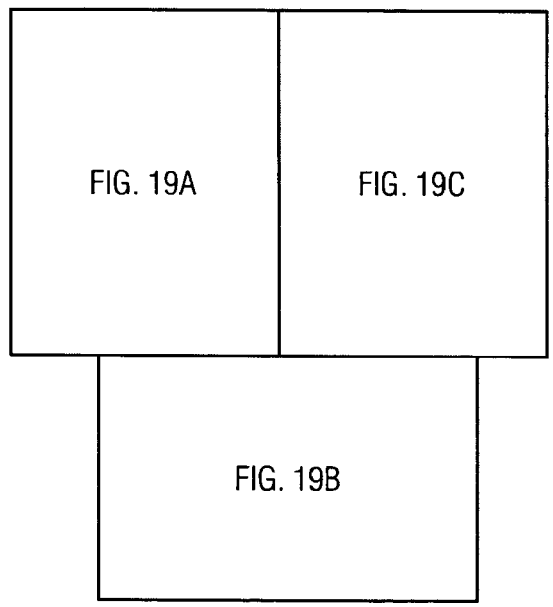
FIGS. 19A, 19B, and 19C provide a flowchart showing the sequence of operational steps for one embodiment of the present invention.
Figure 19A:
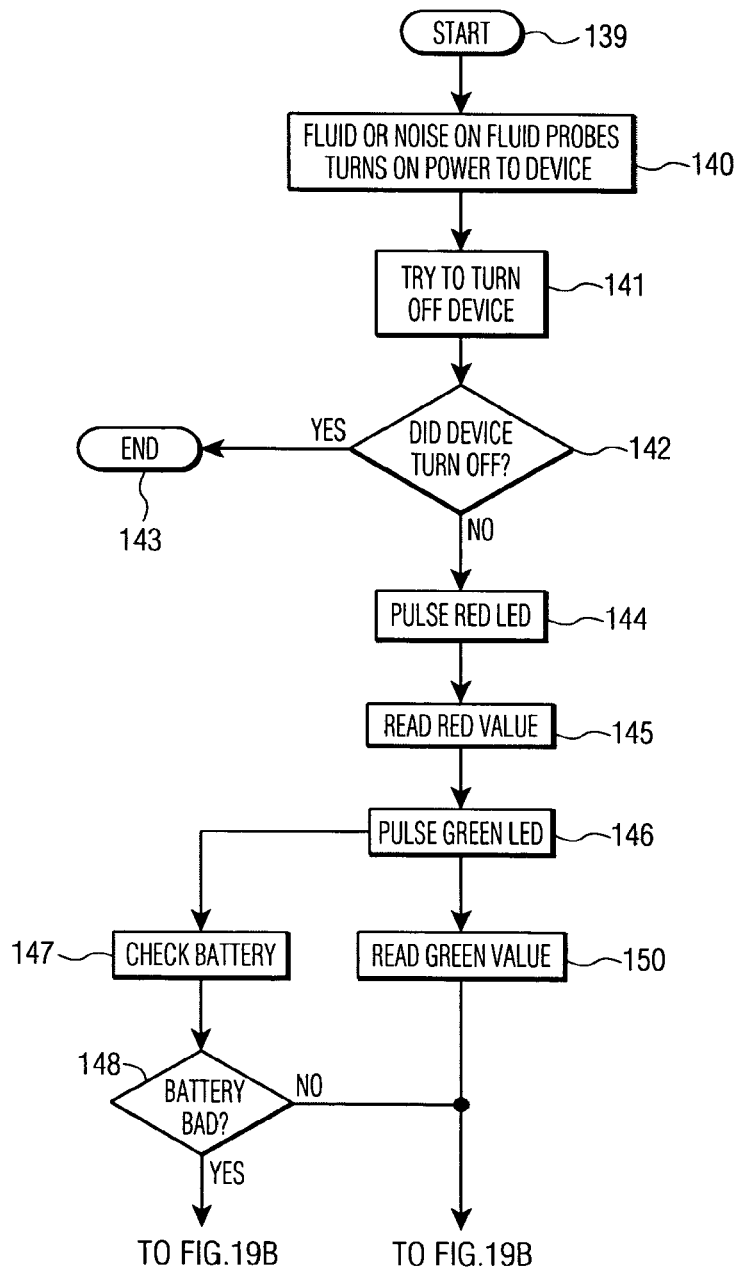
Figure 19B:
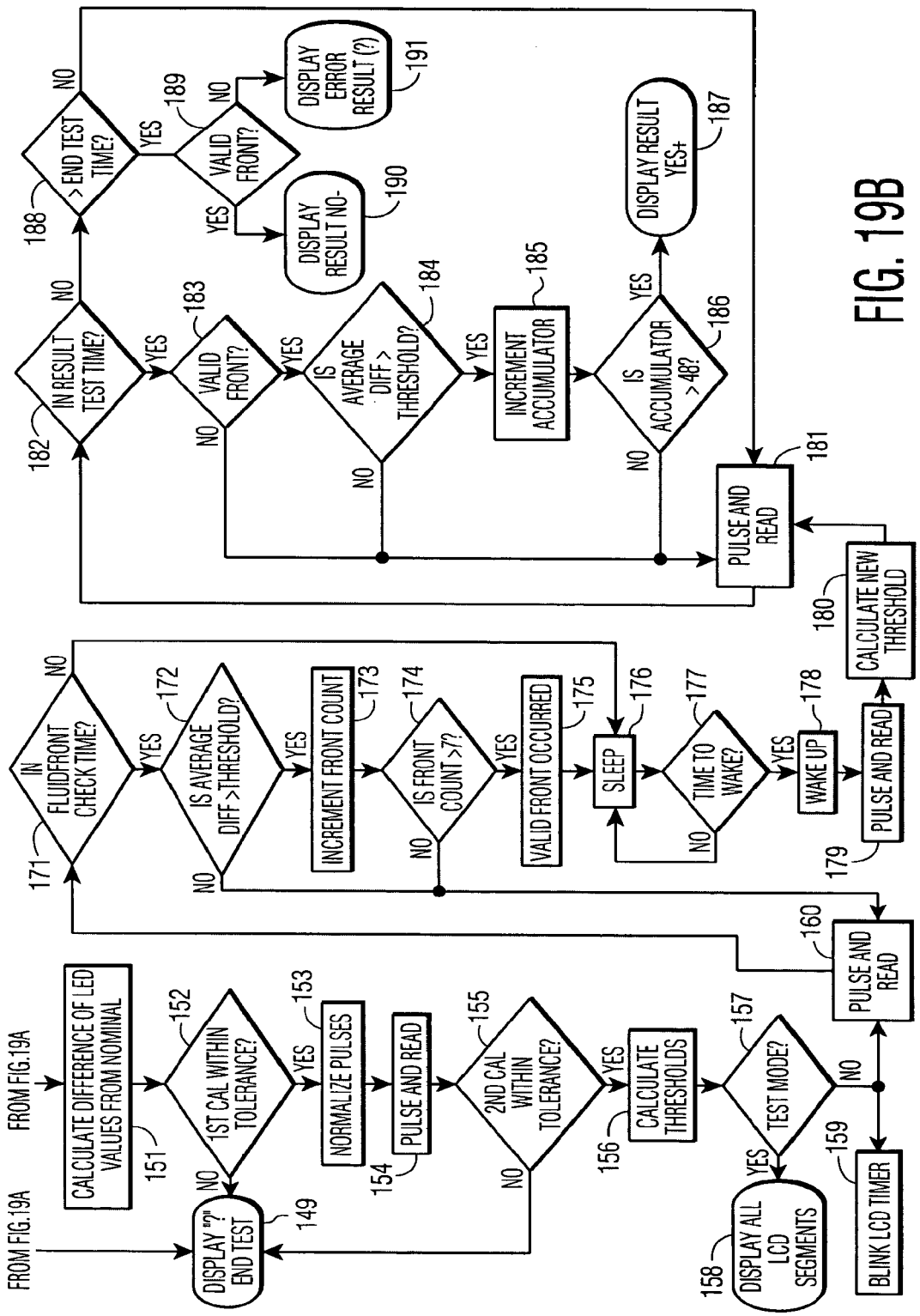
Figure 19C:
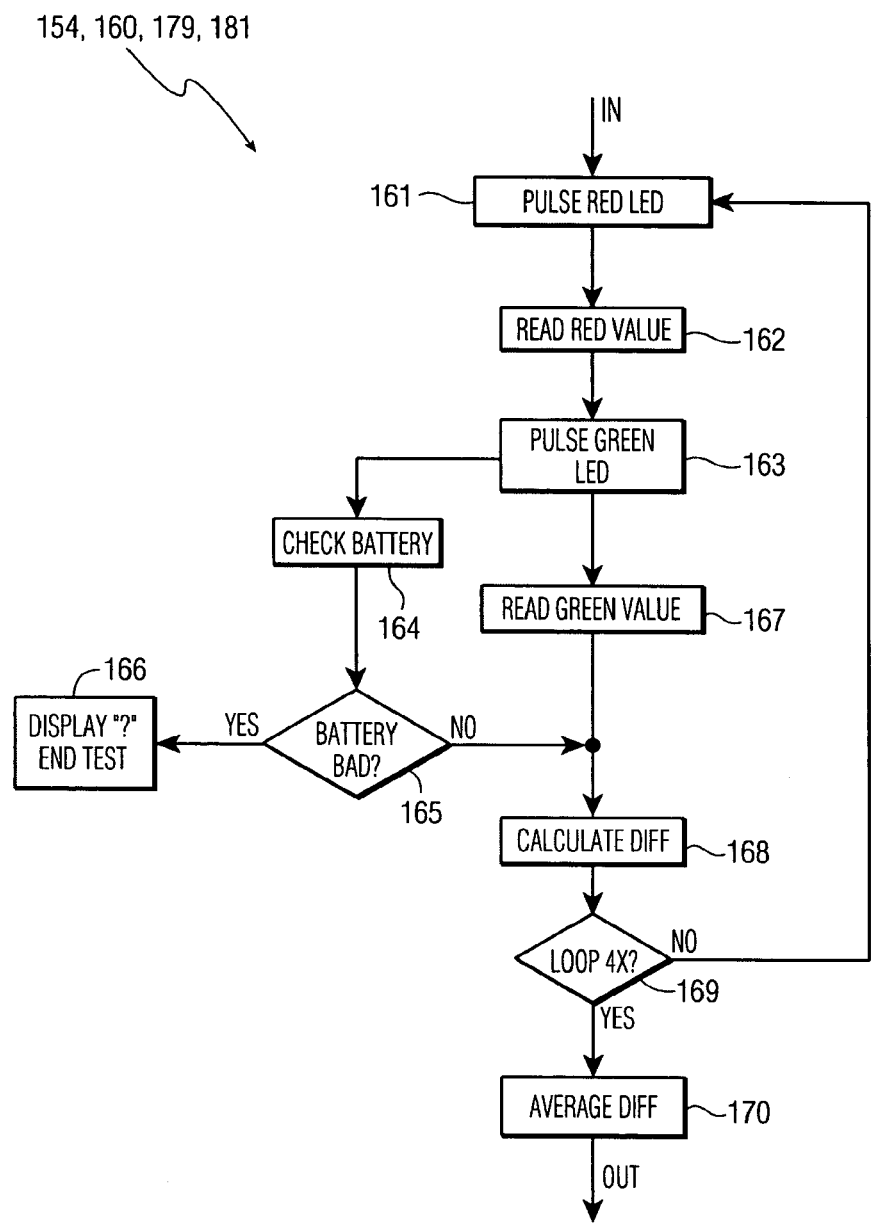

A flowchart is shown in FIGS. 19A, 19B, and 19C of the processing steps required for operation of the device 1. These steps will be described in association with the waveform and timing diagrams of FIGS. 20 and 21. With reference to the flowchart of FIGS. 19A, 19B, and 19C, steps 139 through 191 are shown and briefly described therein in each step relative to the functions of each. More specifically, the Start Step 139 is initiated by a user removing the cap 15, and placing the sample wick 17 into a urine stream for wetting the same with urine. Next, in Step 140 a pair of spaced apart electrical contacts 72, 74 on the PC board 45 which touch the transverse surface of the test strip 39 are wetted by the urine, causing a current flow between the contacts or electrodes 72, 74 which are included in the Fluid Detector 117 shown in FIG. 18. The Debounce Circuit 119 responds to the current flow between the electrodes to apply power to the Power Supply 113 via a shared field effect transistor (FET, not shown) between the Power Supply 113 and the Debounce Circuit 119. The Power Supply 113 turns on, and in turn applies full power to the entire ASIC 111. In Step 141, in this example, for the next 100 ms (milliseconds), the ASIC 111 attempts to try to periodically turn off the device 1 by removing power. If in Step 142 it is determined device 1 is turned off, then Step 143 is entered for the unpowered state via the FET turning off, whereby it is assumed device 1 turned on in error due to noise or some transient effect across electrodes 72, 74. However, if after 100 ms device 1 remains turned on, the ASIC 111 ceases any further attempt to turn the device 1 off, and Step 144 is entered for pulsing red LED 99.

In Step 145, the intensity of the red light emitted is read via photodetector 93, with the value being stored in a register (not shown) in system state machine 121 (see FIG. 18) as a reference or calibration value. Next, in Step 146, the green LED 150 is pulsed for 3.2 ms, in this example. Simultaneously, Step 150 is entered whereby photodetector 93 reads the intensity of the green light emitted, with the value being stored as a reference or calibration value, and Step 147 is entered for checking batteries 47 and 49. If in the next Step 148 the batteries are determined to be "Bad," Step 149 is entered for ending the test and displaying "?" on LCD 13.

If in Step 148, it is determined that batteries 47 and 49 are good, Step 151 is entered for calculating the difference in the intensity of light from the red LED 99 and green LED 105 relative to their expected values which are hardwired in ASIC 111. Next, Step 152 is entered to determine if their respective differences are within a predetermined tolerance. If not, Step 149 is entered to display "?" on LCD 13 and end the test. If both differences are within tolerance, Step 153 is entered for normalizing both pulses associated with their respective differences.

Next, in Step 154, a pulse and read process is entered as shown in FIG. 19B. FIG. 19C shows the steps in detail for the pulse and read Step 154. More specifically, the first step of this process is Step 161 for again pulsing the red LED 99 for 3.2 ms, followed by reading the intensity of the red light emitted in Step 162 and storing the same in a register in the ASIC 111. Next, Step 163 is entered for pulsing the green LED 105 for 3.2 ms, followed by simultaneously entering Step 167 to detect via photodetector 93 the intensity of the green light emitted, and storing the same in a register in the ASIC 111, and checking the batteries 47, 49 in Step 164. If in the following Step 165, the batteries 47, 49, are determined to be "Bad," Step 166 is entered for displaying "?" on the LCD display 13, and ending the test. Contrariwise, if in Step 165, the batteries 47, 49 are determined to be good, Step 168 is entered for calculating the difference between the intensities of the light emitted by the red LED 99 and green LED 105. Following Step 168, Step 169 is entered to determine whether the prior Steps 161 through 165, and 167 through 168 have been performed four times. If not, Step 169 loops back to cause these prior steps to be reentered. If so, Step 170 is entered for calculating the average difference in value between the intensity of light of the red LED 99 and green LED 105. Processing then continues with Step 155 for again calculating the difference in the intensity of light from the red LED 99 and green LED 105 relative to their expected values. If not, Step 149 is entered for displaying "?" on LCD display 13, and ending the test. If within tolerance, Step 156 is entered for calculating thresholds from the red and green intensity values stored in registers in the ASIC 111. Next, Step 157 is entered for determining whether the device 1 has been placed in a test mode. If so, Step 158 is entered for displaying all LCD segments on the LCD display 13. This step is only entered at the factory where each device assembled is tested as previously indicated, with the display of all of the LCD 13 segments alerting a test technician that power should be removed, and no further steps performed, whereby the device 1 has passed the quality control test. Note that during factory testing, the batteries 47 and 49 are not yet installed in the device, an external power is applied to the device, while at the same time the electrical contacts 72 and 74 are shorted to one another for simulating the presence of a conductive fluid, such as urine, for example. After power is removed, the batteries 47 and 49 are installed in the device 1, and the device 1 is completely assembled for packaging and shipment. Also note that during use of the device 1 by the ultimate consumer, that Steps 139 through 157 are performed again, and represent a calibration routine, wherein in Step 157 it is determined that the device 1 is not in a "test mode," causing Steps 159 and 160 to be entered. Step 159 causes a clock icon to blink on and off on the LCD display 13, to let a user know that a test is in progress. Step 160 is entered to cause the "Pulse & Read" process previously described to be repeated. Next, Step 171 is entered to determine if the fluid front check time period has been spent. As shown in FIG. 20, this check time occurs between 5 seconds and 48 seconds of turning on device 1, whereafter a "sleep" or inactivity period State 3 is entered until the end of 127 seconds before data acquisition begins. Note that State 3 can begin anywhere from 12 seconds to 48 seconds depending upon the time of occurrence of the fluid front. If the fluid front check time, that is State 2 (see FIG. 20) is being processed, or has not ended, Step 172 is entered for determining whether the average difference calculated in Step 170 is greater than the threshold previously calculated in Step 156. If not, another process is performed followed by repeating Step 171. If the average difference in intensity is greater than the threshold, Step 173 is entered for incrementing a fluid front counter in ASIC 111, followed by Decision Step 174 for determining whether the count is greater than 7. If not, another "Pulse & Read" process is performed (Step 160). If the count is greater than 7, then Step 175 is entered for indicating that a valid fluid front has occurred. If either 48 seconds or a count greater than 7, for example, has occurred (State 3 in FIG. 20), Step 176 is entered. When it is determined in Step 177 that 127 seconds, in this example, have been spent since turning on device 1, Step 178 will then proceed to "wake up the processing," for entering Step 179 for performing another "Pulse & Read" process. Note that with reference to FIGS. 20 and 21, the device 1 is now in State 4 for beginning data acquisition. Next, Step 180 is entered for calculating new threshold values. The new threshold values represent the reference intensity against which subsequent comparisons are made, as will be described, for using intensity readings from the light emitted by red LED 99 and green LED 105 at a time when the fluid or urine has moved by the capture region 85 on test strip 39. Next, another "Pulse & Read" process is performed in Step 181. In Step 182 it is determined whether the average difference in light intensity obtained from Step 181 is provided within the result allowed test time ranging between 127 to 180 seconds (see FIGS. 20 and 21), Step 183 is entered if the time is still within this range, for testing whether a valid fluid front has been previously detected. If not, Step 181 is repeated for performing another "Pulse & Read," whereas if a valid fluid front was detected, Step 184 is entered for determining whether the average difference in light intensity is greater than a predetermined threshold. If not, Step 181 is reentered, whereas if so, Step 185 is entered for incrementing an accumulator in ASIC 111, followed by entering Step 186 for determining whether the aforesaid accumulator has attained a count greater than 48. If not, Step 181 is reentered and performed, whereas if so, Step 187 is entered for displaying "YES followed by a + sign" for this example.

If in Step 182, the accumulated test time exceeds 180 seconds, Step 188 is entered to determine whether the test time actually exceeds 180 seconds. If not, Step 181 is entered and performed as previously described, and if so, Step 189 is entered to determine whether a valid fluid front has been previously detected. If so, the ASIC 111 drives the LCD display 13 to display "NO followed by a negative sign" for this example. If a valid fluid front was not detected, Step 191 is entered for displaying on the LCD display 13 "(?)," in this example. Following either one of Steps 187, 190, or 191, the State Machine 121, and the LCD display 13 remain active until the batteries 47, 49 are de-energized.

Obviously, the device 1 can be designed for displaying other than the word Yes for indicating pregnancy, or No for indicating no pregnancy, that is for indicating the presence or absence, respectively, of the preselected analyte. The device 1 can be modified for detecting analytes other than those associated with pregnancy.

In this example, the device 1 is designed to remain powered for at least 30 minutes after the initiation of a test for display purposes. As indicated, the entire test period takes about three minutes. The test results can be displayed for the entire 30 minute activation period. Also note that although it is indicated that the sample wick 17 is inserted into a urine stream for taking a sample, it can also be dipped into urine held in a clean container. The system is a self calibrated device 1. The self calibration is automatically performed when the device is powered up by taking a measurement of the red LED 105 and green LED 99 light emissions and storing the values for later reference. Thereafter, as the testing proceeds, the level of light emissions from the red LED 105 and green LED 99 are adjusted against the reference levels. The device 1 is designed to be at least 99% accurate, for detecting for a positive (YES) answer or result for the presence of at least 25.0 mIU/mL of hCG in the urine, for example.

With reference to the circuit schematic diagram of FIG. 22, the electrical connections of the various components of the device 1 are shown. The application specific integrated circuit (ASIC) 111 is designed to operate the device 1 as previously described. More specifically, the photodetector 93 is a photodiode that is protected by a guard 94. The function of guard 94 is to supply a low impedance voltage equal in potential to the input voltage to ASIC 111 to nullify parasitic capacitance effects, and to supply a low impedance plane to act as a shield for the high impedance input to the ASIC 111. The guard 94 is provided in the printed circuit of the PC board 45, as would be known to one of skill in the art. Resistor 280, connected and parallel with the photodiode 93, serves to provide initial trans-impedance gain of the photo current produced by photodiode 93, and serves to linearize the response of photodiode 93. Capacitor 288 provides a low pass filter function. The liquid crystal display (LCD) 13 is connected as shown, and operated by the ASIC 111 for providing the previously mentioned displays at an appropriate time in the operation of the device 1. The ASIC 111 is connected to the electrical contacts 72 and 74 for sensing the presence of fluid, as previously described. The test point 291 provides for a functional test mode for verifying proper operation of the device 1 during manufacture. Bias resistor 286 serves to provide the internal reference current for ASIC 111. The value of capacitor 284 is selected for determining the frequency of the clock. Capacitor 282 serves to provide a compensation capacitor for the internal voltage regulation for the ASIC 111. The batteries 49 and 47 are connected in series between a source of reference potential, ground in this example, and a voltage supply point designated VBAT, which point is also connected via an AC bypass capacitor 278 to ground.

Although various embodiments of the present invention have been shown and described above, they are not meant to be limiting. Those of skill in the art may recognize certain modifications to the various embodiments, which modifications are meant to be covered by the spirit and scope of the appended claims.

What is claimed is:

1. A diagnostic device for detecting the presence of an analyte in a fluid sample, the device comprising:
   a casing having a display;
   a light shield having:
      a first end and a second end,
      first and second longitudinal rails extending along the sides of the light shield between said first end and said second end;
      a recessed bottom portion of said light shield positioned between said first and second rails; and
      a first and a second passageway extending through said recessed bottom portion of said light shield, wherein said light shield is received in said casing;
   a lateral flow diagnostic strip having a region thereon positioned between said first and second longitudinal rails and directly above said first and second passageways through said recessed bottom portion of said light shield;
   a standoff adjacent to said first and second passageways elevating the lateral flow diagnostic strip above said recessed bottom portion of said light shield;
   a circuit board received in said casing coupled to a top portion of said light shield and positioned with respect to said light shield by one or more alignment pins extending through one or more openings in said circuit board;
   a processor mounted to said circuit board received in said casing;
   at least one light source mounted to said circuit board received in said casing adjacent said first passageway, said at least one light source being operatively coupled to said processor, said first passageway being configured to provide a direct line of sight from said at least one light source to said capture region; and at least one sensor mounted to said circuit board received in said casing adjacent said second passageway, said at least one sensor being operatively coupled to said processor, wherein said lateral flow diagnostic strip is positioned so that a gap exists between said lateral flow diagnostic strip and said first and said second passageways through said recessed bottom portion of said light shield.

2. The device of claim 1, said lateral flow diagnostic strip further comprising a registration recess configured to receive a portion of said light shield to properly align said lateral flow diagnostic strip capture region with at least one of said first and said second passageways.

3. The device of claim 1, wherein
said at least one light source is a light emitting diode; and
said at least one sensor is a photo detector.

4. The device of claim 1, wherein said display is a digital display that is operatively coupled to said printed circuit board.

5. The device of claim 1, wherein said first and second longitudinal rails terminate prior to reaching said light shield first and second ends.

6. The device of claim 1, wherein said lateral flow diagnostic strip rests on said light shield first and second longitudinal rails so that a surface of said lateral flow diagnostic strip is spaced apart from said light shield second surface to form said gap between said lateral flow diagnostic strip and said second surface first and second passageway openings.

7. The device of claim 1, wherein said processor is a software driven processor.

8. The device of claim 1, wherein said processor is a state machine.

9. The device of claim 1, wherein a width of said second passageway is less than a width of said region, and wherein a center point of said region is aligned with a center point of said second passageway.

10. The device of claim 1, wherein the lateral flow strip is positioned such that a portion of the region is perpendicular to a sensing direction of said sensor.

11. A diagnostic device for detecting the presence of an analyte in a fluid sample, the device comprising:

a casing;
a light shield having:
    first and second surfaces, wherein a portion of said second surface is recessed,
    first and second ends, and
    at least one passageway extending between said light shield first and second surfaces, said at least one passageway defining an opening in said light shield first surface and said second surface recess,
wherein said light shield is received in said casing;
a lateral flow diagnostic strip received in said casing adjacent to and above said light shield second surface recess so that a gap exists between a surface of said lateral flow diagnostic strip and said light shield second surface passageway opening;
a processor mounted in said casing;
at least one light emitting diode mounted in said casing and operatively coupled to said processor so that light emitted from said diode is projected on said lateral flow diagnostic strip;
at least one photo detector mounted in said casing and operatively coupled to said processor so that light reflected from said lateral flow diagnostic strip surface is received in said light shield second surface at least one passageway opening and directed to said at least one photo detector, wherein said at least one passageway forms a hollow pyramid shape above said photo detector and is configured to block light not reflected through said second surface recess.

12. The device of claim 11, further comprising a second passageway extending between said light shield first and second surfaces, said second passageway defining an opening is said light shield first surface and said second surface recess, wherein said at least one light emitting diode is mounted adjacent said light shield first surface second passageway so that light is projected onto said lateral flow diagnostic strip.

13. The device of claim 11, wherein said processor is a software driven processor.

* * * * *